(12) United States Patent
Busby et al.

(10) Patent No.: US 9,999,124 B2
(45) Date of Patent: Jun. 12, 2018

(54) TAMPER-RESPONDENT ASSEMBLIES WITH TRACE REGIONS OF INCREASED SUSCEPTIBILITY TO BREAKING

(71) Applicant: INTERNATIONAL BUSINESS MACHINES CORPORATION, Armonk, NY (US)

(72) Inventors: James A. Busby, New Paltz, NY (US); Michael J. Fisher, Poughkeepsie, NY (US); Michael A. Gaynes, Vestal, NY (US); David C. Long, Wappingers Falls, NY (US); Thomas Weiss, Poughkeepsie, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days. days.

(21) Appl. No.: 15/341,108

(22) Filed: Nov. 2, 2016

(65) Prior Publication Data

US 2018/0124915 A1    May 3, 2018

(51) Int. Cl.
*G01N 27/20*    (2006.01)
*H05K 1/02*    (2006.01)
*H05K 1/18*    (2006.01)

(52) U.S. Cl.
CPC .......... *H05K 1/0275* (2013.01); *G01N 27/20* (2013.01); *H05K 1/182* (2013.01)

(58) Field of Classification Search
CPC ... H05K 1/0275; H05K 1/182; G01R 31/2825
See application file for complete search history.

(56) References Cited

U.S. PATENT DOCUMENTS

| 3,165,569 A | 1/1965 | Bright et al. |
| 4,160,503 A | 7/1979 | Ohlbach |
| (Continued) | | |

FOREIGN PATENT DOCUMENTS

| CN | 2014-30639 Y | 3/2010 |
| CN | 10-4346587 A | 2/2015 |
| (Continued) | | |

OTHER PUBLICATIONS

Holm, Ragnar, "Electric Contacts: Theory and Application", Spinger-Verlag, New York, 4th Edition, 1981 (pp. 10-19).
(Continued)

*Primary Examiner* — Jermele M Hollington
*Assistant Examiner* — Alvaro Fortich
(74) *Attorney, Agent, or Firm* — Margaret A. McNamara, Esq.; Kevin P. Radigan, Esq.; Heslin, Rothenberg, Farley & Mesiti, P.C.

(57) ABSTRACT

Tamper-respondent assemblies with regions of increased susceptibility to a tamper event are provided, which include one or more tamper-detect sensors, one or more conductive traces, and an adhesive. The tamper-detect sensor(s) facilitates defining a secure volume about one or more electronic components to be protected, and the conductive trace(s) forms, at least in part, a tamper-detect network of the tamper-respondent assembly. The conductive trace(s) is disposed, at least in part, on the tamper-detect sensor(s). The adhesive contacts the conductive trace(s) on the tamper-detect sensor(s), and is disposed, at least in part, between and couples a surface of the tamper-detect sensor(s) to another surface of the assembly. Together, the tamper-detect sensor(s), conductive trace(s), and adhesive are a subassembly, with the subassembly being configured with multiple regions of increased susceptibility to breaking of the con-
(Continued)

ductive trace(s) with a tamper event through the subassembly.

20 Claims, 14 Drawing Sheets

(56) References Cited

U.S. PATENT DOCUMENTS

| | | |
|---|---|---|
| 4,211,324 A | 7/1980 | Ohlbach |
| 4,324,823 A | 4/1982 | Ray, III |
| 4,496,900 A | 1/1985 | Di Stefano et al. |
| 4,516,679 A | 5/1985 | Simpson et al. |
| 4,593,384 A | 6/1986 | Kleijne |
| 4,609,104 A | 9/1986 | Kasper et al. |
| 4,653,252 A | 3/1987 | Van de Haar et al. |
| 4,677,809 A | 7/1987 | Long et al. |
| 4,691,350 A | 9/1987 | Kleijne et al. |
| 4,807,284 A | 2/1989 | Kleijne |
| 4,811,288 A | 3/1989 | Kleijne et al. |
| 4,860,351 A | 8/1989 | Weingart |
| 4,865,197 A | 9/1989 | Craig |
| 5,009,311 A | 4/1991 | Schenk |
| 5,027,397 A | 6/1991 | Double et al. |
| 5,060,114 A | 10/1991 | Feinberg et al. |
| 5,075,822 A | 12/1991 | Baumler et al. |
| 5,117,457 A | 5/1992 | Comerford et al. |
| 5,159,629 A | 10/1992 | Double et al. |
| 5,185,717 A | 2/1993 | Mori |
| 5,201,868 A | 4/1993 | Johnson |
| 5,201,879 A | 4/1993 | Steele et al. |
| 5,211,618 A | 5/1993 | Stoltz |
| 5,239,664 A | 8/1993 | Verrier et al. |
| 5,389,738 A | 2/1995 | Piosenka et al. |
| 5,406,630 A | 4/1995 | Piosenka et al. |
| 5,506,566 A | 4/1996 | Oldfield et al. |
| 5,568,124 A | 10/1996 | Joyce et al. |
| 5,594,439 A | 1/1997 | Swanson |
| 5,675,319 A | 10/1997 | Rivenberg et al. |
| 5,715,652 A | 2/1998 | Stahlecker |
| 5,761,054 A | 6/1998 | Kuhn |
| 5,813,113 A | 9/1998 | Stewart et al. |
| 5,858,500 A | 1/1999 | MacPherson |
| 5,880,523 A | 3/1999 | Candelore |
| 5,988,510 A | 11/1999 | Tuttle et al. |
| 6,121,544 A | 9/2000 | Petsinger |
| 6,195,267 B1 | 2/2001 | MacDonald, Jr. et al. |
| 6,201,296 B1 | 3/2001 | Fries et al. |
| 6,261,215 B1 | 7/2001 | Imer |
| 6,301,096 B1 | 10/2001 | Wozniczka |
| 6,384,397 B1 | 5/2002 | Takiar et al. |
| 6,424,954 B1 | 7/2002 | Leon |
| 6,438,825 B1 | 8/2002 | Kuhn |
| 6,469,625 B1 | 10/2002 | Tomooka |
| 6,473,995 B2 | 11/2002 | Miyakawa et al. |
| 6,512,454 B2 | 1/2003 | Miglioli et al. |
| 6,686,539 B2 | 2/2004 | Farquhar et al. |
| 6,746,960 B2 | 6/2004 | Goodman et al. |
| 6,798,660 B2 | 9/2004 | Moss et al. |
| 6,853,093 B2 | 2/2005 | Cohen et al. |
| 6,879,032 B2 | 4/2005 | Rosenau et al. |
| 6,929,900 B2 | 8/2005 | Farquhar et al. |
| 6,946,960 B2 | 9/2005 | Sisson et al. |
| 6,957,345 B2 | 10/2005 | Cesana et al. |
| 6,970,360 B2 | 11/2005 | Sinha |
| 6,985,362 B2 | 1/2006 | Mori et al. |
| 6,991,961 B2 | 1/2006 | Hubbard et al. |
| 6,996,953 B2 | 2/2006 | Perreault et al. |
| 7,005,733 B2 | 2/2006 | Kommerling et al. |
| 7,015,823 B1 | 3/2006 | Gillen et al. |
| 7,054,162 B2 | 5/2006 | Benson et al. |
| 7,057,896 B2 | 6/2006 | Matsuo et al. |
| 7,094,143 B2 | 8/2006 | Wolm et al. |
| 7,094,459 B2 | 8/2006 | Takahashi |
| 7,095,615 B2 | 8/2006 | Nichols |
| 7,156,233 B2 | 1/2007 | Clark et al. |
| 7,180,008 B2 | 2/2007 | Heitmann et al. |
| 7,189,360 B1 | 3/2007 | Ho et al. |
| 7,214,874 B2 | 5/2007 | Dangler et al. |
| 7,247,791 B2 | 7/2007 | Kulpa |
| 7,304,373 B2 | 12/2007 | Taggart et al. |
| 7,310,737 B2 | 12/2007 | Patel et al. |
| 7,465,887 B2 | 12/2008 | Suzuki et al. |
| 7,475,474 B2 | 1/2009 | Heitmann et al. |
| 7,515,418 B2 | 4/2009 | Straznicky et al. |
| 7,549,064 B2 | 6/2009 | Elbert et al. |
| 7,640,658 B1 | 1/2010 | Pham et al. |
| 7,643,290 B1 | 1/2010 | Narasimhan et al. |
| 7,663,883 B2 | 2/2010 | Shirakami et al. |
| 7,672,129 B1 | 3/2010 | Ouyang et al. |
| 7,731,517 B2 | 6/2010 | Lee et al. |
| 7,746,657 B2 | 6/2010 | Oprea et al. |
| 7,760,086 B2 | 7/2010 | Hunter et al. |
| 7,768,005 B2 | 8/2010 | Condorelli et al. |
| 7,783,994 B2 | 8/2010 | Ball et al. |
| 7,787,256 B2 | 8/2010 | Chan et al. |
| 7,868,411 B2 | 1/2011 | Kim et al. |
| 7,898,413 B2 | 3/2011 | Hsu et al. |
| 7,901,977 B1 | 3/2011 | Angelopoulos et al. |
| 7,947,911 B1 | 5/2011 | Pham et al. |
| 7,978,070 B2 | 7/2011 | Hunter |
| 8,006,101 B2 | 8/2011 | Crawford |
| 8,084,855 B2 | 12/2011 | Lower et al. |
| 8,094,450 B2 | 1/2012 | Cole |
| 8,101,267 B2 | 1/2012 | Samuels et al. |
| 8,133,621 B2 | 3/2012 | Wormald et al. |
| 8,199,506 B2 | 6/2012 | Janik et al. |
| 8,287,336 B2 | 10/2012 | Dangler et al. |
| 8,325,486 B2 | 12/2012 | Arshad et al. |
| 8,516,269 B1 | 8/2013 | Hamlet et al. |
| 8,589,703 B2 | 11/2013 | Lee et al. |
| 8,646,108 B2 | 2/2014 | Shiakallis et al. |
| 8,659,506 B2 | 2/2014 | Nomizo |
| 8,659,908 B2 | 2/2014 | Adams et al. |
| 8,664,047 B2 | 3/2014 | Lower et al. |
| 8,716,606 B2 | 5/2014 | Kelley et al. |
| 8,797,059 B2 | 8/2014 | Boday et al. |
| 8,836,509 B2 | 9/2014 | Lowy |
| 8,853,839 B2 | 10/2014 | Gao et al. |
| 8,879,266 B2 | 11/2014 | Jarvis et al. |
| 8,890,298 B2 | 11/2014 | Buer et al. |
| 8,947,889 B2 | 2/2015 | Kelley et al. |
| 8,961,280 B2 | 2/2015 | Dangler et al. |
| 9,003,199 B2 | 4/2015 | Dellmo et al. |
| 9,011,762 B2 | 4/2015 | Seppa et al. |
| 9,052,070 B2 | 6/2015 | Davis et al. |
| 9,166,586 B2 | 10/2015 | Carapelli et al. |
| 9,298,956 B2 | 3/2016 | Wade et al. |
| 2001/0050425 A1 | 12/2001 | Beroz et al. |
| 2001/0056542 A1 | 12/2001 | Cesana et al. |
| 2002/0002683 A1 | 1/2002 | Benson |
| 2002/0068384 A1 | 6/2002 | Beroz et al. |
| 2002/0084090 A1 | 7/2002 | Farquhar |
| 2003/0009684 A1 | 1/2003 | Schwenck et al. |
| 2005/0068735 A1 | 3/2005 | Fissore et al. |
| 2005/0111194 A1 | 5/2005 | Sohn et al. |
| 2005/0180104 A1 | 8/2005 | Olesen et al. |
| 2006/0034731 A1 | 2/2006 | Lewis et al. |
| 2006/0049941 A1 | 3/2006 | Hunter et al. |
| 2006/0072288 A1 | 4/2006 | Stewart et al. |
| 2006/0196945 A1 | 9/2006 | Mendels |
| 2006/0218779 A1 | 10/2006 | Ooba et al. |
| 2007/0064396 A1 | 3/2007 | Oman et al. |
| 2007/0064399 A1 | 3/2007 | Mandel et al. |
| 2007/0108619 A1 | 5/2007 | Hsu |
| 2007/0211436 A1 | 9/2007 | Robinson et al. |
| 2007/0230127 A1 | 10/2007 | Peugh et al. |
| 2007/0268671 A1 | 11/2007 | Brandenburg et al. |
| 2008/0050512 A1 | 2/2008 | Lower et al. |
| 2008/0106400 A1* | 5/2008 | Hunter .............. G06F 21/87 340/540 |
| 2008/0144290 A1 | 6/2008 | Brandt et al. |
| 2008/0159539 A1 | 7/2008 | Huang et al. |
| 2008/0160274 A1 | 7/2008 | Dang et al. |
| 2008/0191174 A1 | 8/2008 | Ehrensvard et al. |

(56) References Cited

U.S. PATENT DOCUMENTS

| | | |
|---|---|---|
| 2008/0251906 A1 | 10/2008 | Eaton et al. |
| 2009/0040735 A1* | 2/2009 | Chan .................. G06F 21/87 361/748 |
| 2009/0073659 A1 | 3/2009 | Peng et al. |
| 2009/0166065 A1 | 7/2009 | Clayton et al. |
| 2010/0088528 A1 | 4/2010 | Sion |
| 2010/0110647 A1 | 5/2010 | Hiew et al. |
| 2010/0177487 A1 | 7/2010 | Arshad et al. |
| 2010/0319986 A1 | 12/2010 | Bleau et al. |
| 2011/0001237 A1 | 1/2011 | Brun et al. |
| 2011/0038123 A1 | 2/2011 | Janik et al. |
| 2011/0103027 A1 | 5/2011 | Aoki et al. |
| 2011/0241446 A1 | 10/2011 | Tucholski |
| 2011/0299244 A1 | 12/2011 | Dede et al. |
| 2012/0050998 A1 | 3/2012 | Klum et al. |
| 2012/0117666 A1 | 5/2012 | Oggioni et al. |
| 2012/0140421 A1 | 6/2012 | Kirstine et al. |
| 2012/0319986 A1 | 6/2012 | Toh et al. |
| 2012/0170217 A1 | 7/2012 | Nishikimi et al. |
| 2012/0185636 A1 | 7/2012 | Leon et al. |
| 2012/0244742 A1 | 9/2012 | Wertz et al. |
| 2012/0256305 A1 | 10/2012 | Kaufmann et al. |
| 2012/0320529 A1 | 12/2012 | Loong et al. |
| 2013/0033818 A1 | 2/2013 | Hosoda et al. |
| 2013/0058052 A1 | 3/2013 | Arshad et al. |
| 2013/0104252 A1 | 4/2013 | Yanamadala et al. |
| 2013/0141137 A1 | 6/2013 | Krutzik et al. |
| 2013/0158936 A1 | 6/2013 | Rich et al. |
| 2013/0170217 A1 | 7/2013 | Lee |
| 2013/0208422 A1 | 8/2013 | Hughes et al. |
| 2013/0235527 A1 | 9/2013 | Wagner et al. |
| 2013/0283386 A1 | 10/2013 | Lee |
| 2014/0022733 A1 | 1/2014 | Lim et al. |
| 2014/0160679 A1 | 6/2014 | Kelty et al. |
| 2014/0184263 A1 | 7/2014 | Ehrenpfordt et al. |
| 2014/0204533 A1 | 7/2014 | Abeyasekera et al. |
| 2014/0321064 A1 | 10/2014 | Bose et al. |
| 2014/0325688 A1 | 10/2014 | Cashin et al. |
| 2015/0007427 A1 | 1/2015 | Dangler et al. |
| 2015/0163933 A1 | 6/2015 | Steiner |
| 2015/0235053 A1 | 8/2015 | Lee et al. |
| 2015/0373487 A1* | 12/2015 | Miller .................. H04W 4/02 455/456.1 |
| 2016/0005262 A1 | 1/2016 | Hirato et al. |
| 2016/0137548 A1 | 5/2016 | Cabral, Jr. et al. |
| 2016/0262253 A1 | 9/2016 | Isaacs et al. |
| 2016/0262270 A1 | 9/2016 | Isaacs et al. |
| 2017/0019987 A1 | 1/2017 | Dragone et al. |

FOREIGN PATENT DOCUMENTS

| | | |
|---|---|---|
| DE | 19816571 A1 | 10/1999 |
| DE | 19816572 A1 | 10/1999 |
| DE | 10-2012-203955 A1 | 9/2013 |
| EP | 0 056 360 A1 | 10/1993 |
| EP | 0 629 497 A2 | 12/1994 |
| EP | 1 184 773 A1 | 3/2002 |
| EP | 1 207 444 A2 | 5/2002 |
| EP | 1 734 578 A1 | 12/2006 |
| EP | 1 968 362 A2 | 9/2008 |
| EP | 2 104 407 A1 | 9/2009 |
| EP | 1 672 464 B1 | 4/2012 |
| EP | 2 560 467 A1 | 2/2013 |
| JP | 61-297035 A | 12/1986 |
| JP | 2000-238141 A | 9/2000 |
| JP | 2013-125807 A | 6/2013 |
| JP | 2013-140112 A | 7/2013 |
| WO | WO 1999/003675 A1 | 1/1999 |
| WO | WO 1999/021142 A1 | 4/1999 |
| WO | WO 2001/063994 A2 | 8/2001 |
| WO | WO 2003/012606 A2 | 2/2003 |
| WO | WO 2003/025080 A1 | 3/2003 |
| WO | WO 2004/040505 A1 | 5/2004 |
| WO | WO 2009/042335 A1 | 4/2009 |
| WO | WO 2009/092472 A1 | 7/2009 |
| WO | WO 2010/128939 A1 | 11/2010 |
| WO | WO 2013/004292 A1 | 1/2013 |
| WO | WO 2013/189483 A1 | 12/2013 |
| WO | WO 2014/086987 A2 | 6/2014 |
| WO | WO 2014/158159 A1 | 10/2014 |

OTHER PUBLICATIONS

Clark, Andrew J., "Physical Protection of Cryptographic Devices", Advanced in Cyprtology, Eurocrypt '87, Springer, Berlin Heidelberg (1987) (11 pages).

Halperin et al., "Latent Open Testing of Electronic Packaging", MCMC-194, IEEE (1994) (pp. 83-33).

Simek, Bob, "Tamper Restrictive Thermal Ventilation System for Enclosures Requiring Ventilation and Physical Security", IBM Publication No. IPCOM000008607D, Mar. 1, 1998 (2 pages).

Pamula et al., "Cooling of Integrated Circuits Using Droplet-Based Microfluidics", Association for Computing Machinery (ACM), GLSVLSI'03, Apr. 28-29, 2003 (pp. 84-87).

Saran et al., "Fabrication and Characterization of Thin Films of Single-Walled Carbon Nanotube Bundles on Flexible Plastic Substrates", Journal of the American Chemical Society, vol. 126, No. 14 (Mar. 23, 2004) (pp. 4462-4463).

Khanna P.K. et al., "Studies on Three-Dimensional Moulding, Bonding and Assembling of Low-Temperature-Cofired Ceramics MEMS and MST Applications." Materials Chemistry and Physics, vol. 89, No. 1 (2005) (pp. 72-79).

Drimer et al., "Thinking Inside the Box: System-Level Failures of Tamper Proofing", 2008 IEEE Symposium on Security and Privacy, (Feb. 2008) (pp. 281-295).

Loher et al., "Highly Integrated Flexible Electronic Circuits and Modules", 3rd International IEEE on Microsystems, Packaging, Assembly & Circuits Technology Conference (Oct. 22-24, 2008) (Abstract Only) (1 page).

Sample et al., "Design of an RFID-Based Battery-Free Programmable Sensing Platform", IEEE Transactions on Instrumentation and Measurement, vol. 57, No. 11, Nov. 2008 (pp. 2608-2615).

Jhang et al., "Nonlinear Ultrasonic Techniques for Non-Destructive Assessment of Micro Damage in Material: A Review", International Journal of Prec. Eng. & Manuf., vol. 10, No. 1, Jan. 2009 (pp. 123-135).

Anonymous, "Consolidated Non-Volatile Memory in a Chip Stack", IBM Technical Disclosure: IP.com No. IPCOM000185250, Jul. 16, 2009 (6 pages).

Isaacs et al., "Tamper Proof, Tamper Evident Encryption Technology", Pan Pacific Symposium SMTA Proceedings (2013) (9 pages).

Anonymous, "Selective Memory Encryption", IBM Technical Disclosure: IP.com IPCOM000244183, Nov. 20, 2015 (6 pages).

Zhou et al., "Nonlinear Analysis for Hardware Trojan Detection", ICSPCC2015, IEEE (2015) (4 pages).

Harting Mitronics, "Saftey Caps for Payment Terminals", http://harting-mitronics.ch/fileadmin/hartingmitronics/case_studies/Saftey_caps_for_payment terminals.pdf, downloaded Aug. 2016 (2 pages).

Dangler et al., "Tamper-Respondent Sensors with Formed Flexible Layer(s)", U.S. Appl. No. 14/865,551, filed Sep. 25, 2015 (113 pages).

Brodsky et al., "Overlapping, Discrete Tamper-Respondent Sensors", U.S. Appl. No. 14/865,572, filed Sep. 25, 2015 (114 pages).

Dangler et al., "Tamper-Respondent Assemblies with Region(s) of Increased Susceptibility to Damage", U.S. Appl. No. 14/865,591, filed Sep. 25, 2015 (114 pages).

Brodsky et al., "Circuit Boards and Electronic Packages with Embedded Tamper-Respondent Sensor", U.S. Appl. No. 14/865,610, filed Sep. 25, 2015 (43 pages).

Brodsky et al, "Tamper-Respondent Assemblies", U.S. Appl. No. 14/865,632, filed Sep. 25, 2015 (115 pages).

Brodksy et al., "Enclosure with Inner Tamper-Respondent Sensor(s)", U.S. Appl. No. 14/865,651, filed Sep. 25, 2015 (115 pages).

(56) References Cited

OTHER PUBLICATIONS

Fisher et al., "Enclosure with Inner Tamper-Respondent Sensor(s) and Physical Security Element(s)", U.S. Appl. No. 14/865,686, filed Sep. 25, 2015 (114 pages).
Brodsky et al., "Tamper-Respondent Assemblies with Bond Protection", U.S. Appl. No. 14/865,708, filed Sep. 25, 2015 (113 pages).
Brodsky et al., "Circuit Layouts of Tamper-Respondent Sensors", U.S. Appl. No. 14/886,179, filed Oct. 19, 2015 (113 pages).
Isaacs, Phillip Duane, "Tamper-Respondent Assembly with Protective Wrap(s) Over Tamper-Respondent Sensor(s)", U.S. Appl. No. 14/918,691, filed Oct. 21, 2015 (40 pages).
Brodsky et al., "Tamper-Respondent Assemblies with Bond Protection", U.S. Appl. No. 14/941,860, filed Nov. 16, 2015 (108 pages).
Fisher et al., "Enclosure with Inner Tamper-Respondent Sensor(s) and Physical Security Element(s)", U.S. Appl. No. 14/941,872, filed Nov. 16, 2015 (109 pages).
Brodsky et al, "Tamper-Respondent Assemblies", U.S. Appl. No. 14/941,887, filed Nov. 16, 2015 (109 pages).
Brodsky et al., "Circuit Boards and Electronic Packages with Embedded Tamper-Respondent Sensors", U.S. Appl. No. 14/941,908, filed Nov. 16, 2015 (41 pages).
Fisher et al., "Tamper-Respondent Assembly with Vent Structure", U.S. Appl. No. 14/955,283, filed Dec. 1, 2015 (61 pages).
Fisher et al., "Applying Pressure to Adhesive Using CTE Mismatch Between Components", U.S. Appl. No. 14/963,681, filed Dec. 9, 2015 (68 pages).
Brodsky et al., "Tamper-Respondent Assemblies with Enclosure-to-Board Protection", U.S. Appl. No. 14/974,036, filed Dec. 18, 2015 (55 pages).
Busby et al., "Multi-Layer Stack with Embedded Tamper-Detect Protection", U.S. Appl. No. 15/053,336, filed Feb. 25, 2016 (68 pages).
Campbell et al., "Tamper-Proof Electronic Packages With Two-Phase Dielectric Fluid", U.S. Appl. No. 15/139,503, filed Apr. 27, 2016 (60 pages).
Busby et al., "Tamper-Proof Electronic Packages Formed With Stressed Glass", U.S. Appl. No. 15/154,077, filed May 13, 2016 (45 pages).
Busby et al., "Tamper-Proof Electronic Packages With Stressed Glass Component Substrate(s)", U.S. Appl. No. 15/154,088, filed May 13, 2016 (56 pages).
Brodsky et al., "Circuit Layouts of Tamper-Respondent Sensors", U.S. Appl. No. 15/187,002, filed Jun. 20, 2016 (110 pages).
Brodsky et al., "Tamper-Respondent Assemblies with Enclosure-to-Board Protection", U.S. Appl. No. 15/193,525, filed Jun. 27, 2016 (54 pages).
Fisher et al., "Applying Pressure to Adhesive Using CTE Mismatch Between Components", U.S. Appl. No. 15/193,556, filed Jun. 27, 2016 (71 pages).
Busby et al., "Tamper-Respondent Assembly with Nonlinearity Monitoring", U.S. Appl. No. 15/194,738, filed Jun. 28, 2016 (48 pages).
Dangler et al., "Tamper-Respondent Sensors with Formed Flexible Layer(s)", U.S. Appl. No. 15/249,663, filed Aug. 29, 2016 (109 pages).
Brodsky et al., "Overlapping, Discrete Tamper-Respondent Sensors", U.S. Appl. No. 15/249,671, filed Aug. 29, 2016 (109 pages).
Dangler et al., "Tamper-Respondent Assemblies with Region(s) of Increased Susceptibility to Damage", U.S. Appl. No. 15/249,676, filed Aug. 29, 2016 (110 pages).
Dragone et al., "Tamper-Respondent Assembly with Sensor Connection Adapter", U.S. Appl. No. 15/268,959, filed Sep. 19, 2016 (45 pages).
Dragone et al., "Vented Tamper-Respondent Assemblies", U.S. Appl. No. 15/275,748, filed Sep. 26, 2016 (53 pages).
Dragone et al., "Tamper-Respondent Assemblies with In Situ Vent Structure(s)", U.S. Appl. No. 15/275,762, filed Sep. 26, 2016 (72 pages).
Fisher et al., Office Action for U.S. Appl. No. 14/865,686, filed Sep. 25, 2015, dated Jun. 29, 2016 (17 pages).
Brodsky et al., Office Action for U.S. Appl. No. 14/865,651, filed Sep. 25, 2015, dated Jul. 13, 2016 (10 pages).
Brodsky et al., "Enclosure with Inner Tamper-Respondent Sensor(s)", U.S. Appl. No. 15/409,851, filed Jan. 19, 2017 (115 pages).
Brodsky et al., "Tamper-Respondent Assemblies with Enclosure-to-Board Protection", U.S. Appl. No. 15/423,833, filed Feb. 3, 2017 (54 pages).

\* cited by examiner

TAMPER-RESPONDENT ASSEMBLIES WITH TRACE REGIONS OF INCREASED SUSCEPTIBILITY TO BREAKING

BACKGROUND

Many activities require secure electronic communications. To facilitate secure electronic communications, an encryption/decryption system may be implemented on an electronic assembly or printed circuit board assembly that is included in equipment connected to a communications network. Such an electronic assembly is an enticing target for malefactors since it may contain codes or keys to decrypt intercepted messages, or to encode fraudulent messages. To prevent this, an electronic assembly may be mounted in an enclosure, which is then wrapped in a security sensor and encapsulated with polyurethane resin. A security sensor may be, in one or more embodiments, a web or sheet of insulating material with circuit elements, such as closely-spaced, conductive lines fabricated on it. The circuit elements are disrupted if the sensor is torn, and the tear can be sensed in order to generate an alarm signal. The alarm signal may be conveyed to a monitor circuit in order to reveal an attack on the integrity of the assembly. The alarm signal may also trigger an erasure of encryption/decryption keys stored within the electronic assembly.

SUMMARY

Provided herein, in one or more aspects, is a tamper-respondent assembly which includes: a tamper-detect sensor, at least one conductive trace, and an adhesive. The tamper-detect sensor facilitates defining a secure volume about at least one electronic component to be protected, and the at least one conductive trace forms, at least in part, at least one tamper-detect network of the tamper-respondent assembly. The at least one conductive trace is exposed, at least in part, on the tamper-detect sensor. The adhesive contacts the at least one conductive trace on the at least one tamper-detect sensor, and is disposed, at least in part, between and couples a surface of the tamper-detect sensor to another surface of the tamper-respondent assembly. Together, the tamper-detect sensor, at least one conductive trace, and adhesive are a subassembly of the tamper-respondent assembly, and the subassembly is configured with multiple regions of increased susceptibility to breaking of the at least one conductive trace with a tamper event through the subassembly.

In one or more other aspects, a tamper-respondent assembly is provided which includes: an electronic enclosure, a tamper-detect sensor, at least one conductive trace, and an adhesive. The electronic enclosure is to enclose, at least in part, at least one electronic component to be protected, and includes an inner surface. The tamper-detect sensor, which includes at least one flexible layer with tamper-detect circuit lines, covers, at least in part, the inner surface of the electronic enclosure and facilitates defining a secure volume about the at least one electronic component. The at least one conductive trace forms, at least in part, at least one tamper-detect network of the tamper-respondent assembly, and is exposed, at least in part, on the tamper-detect sensor. The adhesive contacts the at least one conductive trace on the at least one tamper-detect sensor, and is disposed, at least in part, between and couples a surface of the tamper-detect sensor to another surface of the tamper-respondent assembly. Together, the tamper-detect sensor, at least one conductive trace, and adhesive are a subassembly of the tamper-respondent assembly, and the subassembly is configured with multiple regions of increased susceptibility to breaking of the at least one conductive trace with a tamper event through the subassembly.

In one or more further aspects, a fabrication method is provided which includes fabricating a tamper-respondent assembly. The fabricating of the tamper-respondent assembly includes: providing a tamper-detect sensor to facilitate defining a secure volume about at least one electronic component to be protected; providing at least one conductive trace forming, at least in part, at least one tamper-detect network of the tamper-respondent assembly, the at least one conductive trace being disposed, at least in part, on the tamper-detect sensor; providing an adhesive contacting the at least one conductive trace on the tamper-detect sensor, the adhesive being disposed, at least in part, between and coupling a surface of the tamper-detect sensor to another surface of the tamper-respondent assembly; and the tamper-detect sensor, at least one conductive trace, and adhesive being a subassembly of the tamper-respondent assembly, the subassembly being configured with multiple regions of increased susceptibility to breaking of the at least one conductive trace with a tamper event through the subassembly.

Additional features and advantages are realized through the techniques of the present invention. Other embodiments and aspects of the invention are described in detail herein and are considered a part of the claimed invention.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following detailed description taken in conjunction with the accompanying drawings in which:

DETAILED DESCRIPTION

Aspects of the present invention and certain features, advantages, and details thereof, are explained more fully below with reference to the non-limiting example(s) illustrated in the accompanying drawings. Descriptions of well-known materials, fabrication tools, processing techniques, etc., are omitted so as not to unnecessarily obscure the invention in detail. It should be understood, however, that the detailed description and the specific example(s), while indicating aspects of the invention, are given by way of illustration only, and are not by way of limitation. Various substitutions, modifications, additions, and/or arrangements, within the spirit and/or scope of the underlying inventive concepts will be apparent to those skilled in the art for this disclosure. Note further that reference is made below to the drawings, which are not drawn to scale for ease of understanding, wherein the same reference numbers used throughout different figures designate the same or similar components. Also, note that numerous inventive aspects and features are disclosed herein, and unless otherwise inconsistent, each disclosed aspect or feature is combinable with any other disclosed aspect or feature as desired for a particular application, for instance, for establishing a secure volume about an electronic component(s) or electronic assembly to be protected.

Figure 1:
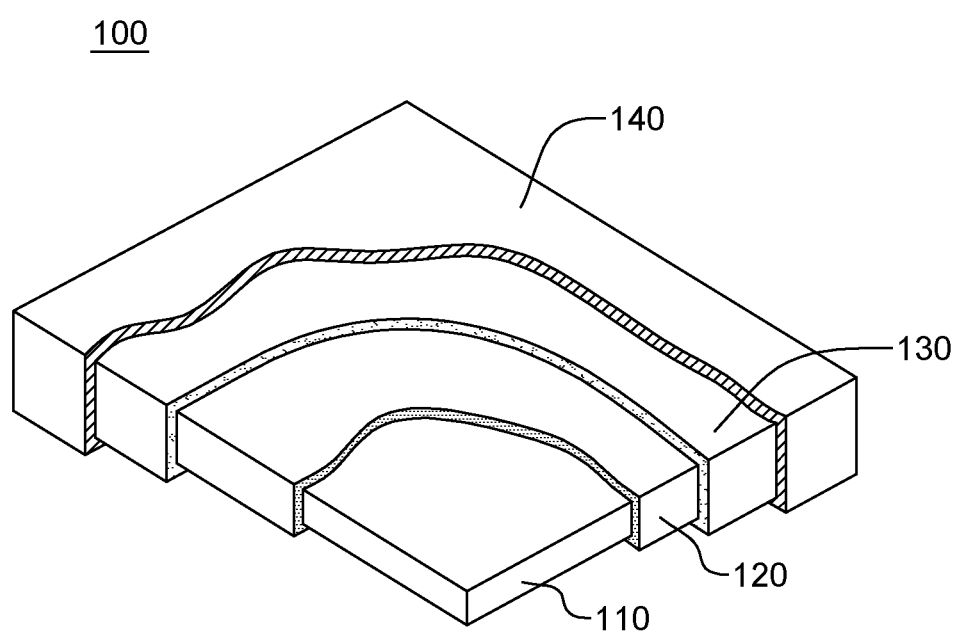
FIG. 1 is a partial cut-away of one embodiment of a tamper-proof electronic package.

Reference is first made to FIG. 1, which illustrates one approach for an electronic package 100 configured as a tamper-proof electronic package for purposes of discussion. In the depicted embodiment, an electronic assembly enclosure 110 is provided containing, for instance, an electronic assembly, which in one embodiment may include a plurality of electronic components, such as an encryption and/or decryption module and associated memory. The encryption and/or decryption module may include security-sensitive information with, for instance, access to the information stored in the module requiring use of a variable key, and with the nature of the key being stored in the associated memory within the enclosure.

In one or more implementations, a tamper-proof electronic package or tamper-respondent assembly, such as depicted, is configured or arranged to detect attempts to tamper with or penetrate into electronic assembly enclosure 110. Accordingly, electronic assembly enclosure 110 also includes, for instance, a monitor circuit which, if tampering is detected, activates an erase circuit to erase information stored within the associated memory, as well as the encryption and/or decryption module within the communications card. These components may be mounted on, and interconnected by, a multilayer circuit board, such as a printed circuit board or other multilayer substrate, and be internally or externally powered via a power supply provided within the electronic assembly enclosure.

In the embodiment illustrated, and as one example only, electronic assembly enclosure 110 may be surrounded by a tamper-detect sensor 120, an encapsulant 130, and an outer, thermally conductive enclosure 140. In one or more implementations, tamper-detect sensor 120 may include a tamper-detection laminate that is folded around electronic assembly enclosure 110, and encapsulant 130 may be provided in the form of a molding. Tamper-detect sensor 120 may include various detection layers, which are monitored through, for instance, a ribbon cable by the enclosure monitor, against attempts to penetrate enclosure 110 and damage the enclosure monitor or erase circuit, before information can be erased from the encryption module. The tamper-detect sensor may be, for example, any such article commercially available or described in various publications and issued patents, or any enhanced article such as disclosed herein.

By way of example, tamper-detect sensor 120 may be formed as a tamper-detection laminate including a number of separate layers with, for instance, an outermost lamination-detection layer including a matrix of, for example, diagonally-extending or sinusoidally-extending, conductive or semi-conductive lines printed onto a regular, thin insulating film. The matrix of lines forms a number of continuous conductors which would be broken if attempts are made to penetrate the film. The lines may be formed, for instance, by printing conductive traces onto the film and selectively connecting the lines on each side, by conductive vias, near the edges of the film. Connections between the lines and an enclosure monitor of the communications card may be provided via, for instance, one or more ribbon cables. The ribbon cable itself may be formed of lines of conductive material printed onto an extension of the film, if desired. Connections between the matrix and the ribbon cable may be made via connectors formed on one edge of the film. As noted, the laminate may be wrapped around the electronic assembly enclosure to define the tamper-detect sensor 120 surrounding enclosure 110.

In one or more implementations, the various elements of the laminate may be adhered together and wrapped around enclosure 110, in a similar manner to gift-wrapping a parcel, to define the tamper-detect sensor shape 120. The assembly may be placed in a mold which is then filled with, for instance, cold-pour polyurethane, and the polyurethane may be cured and hardened to form an encapsulant 130. The encapsulant may, in one or more embodiments, completely surround the tamper-detect sensor 120 and enclosure 110, and thus form a complete environmental seal, protecting the interior of the enclosure. The hardened polyurethane is resilient and increases robustness of the electronic package in normal use. Outer, thermally conductive enclosure 140 may optionally be provided over encapsulant 130 to, for instance, provide further structural rigidity to the electronic package.

When considering tamper-proof packaging, the electronic package needs to maintain defined tamper-proof requirements, such as those set forth in the National Institutes of Standards and Technology (NIST) Publication FIPS 140-2, which is a U.S. Government Computer Security Standard, used to accredit cryptographic modules. The NIST FIPS 140-2 defines four levels of security, named Level 1 to Level 4, with Security Level 1 providing the lowest level of security, and Security Level 4 providing the highest level of security. At Security Level 4, physical security mechanisms are provided to establish a complete envelope of protection around the cryptographic module, with the intent of detecting and responding to any unauthorized attempt at physical access. Penetration of the cryptographic module enclosure from any direction has a very high probability of being detected, resulting in the immediate zeroization of all plain text critical security parameters (CSPs). Security Level 4 cryptographic modules are useful for operation in physically unprotected environments. Security Level 4 also protects a cryptographic module against a security compromise due to environmental conditions or fluctuations outside the module's normal operating ranges for voltage and temperature. Intentional excursions beyond the normal operating ranges may be used by an attacker to thwart the cryptographic module's defenses. The cryptographic module is also required to either include specialized environmental protection features designed to detect fluctuations and zeroize, critical security parameters, or to undergo rigorous environmental failure testing to provide reasonable assurances that the module will not be affected by fluctuations outside the normal operating range in a manner than can compromise the security of the module.

To address the demands for ever-improving anti-intrusion technology, and the higher-performance encryption/decryption functions being provided, enhancements to the tamper-proof, tamper-evident packaging for the electronic component(s) or assembly at issue are desired.

Numerous enhancements are described herein to, for instance, tamper-proof electronic packages or tamper-respondent assemblies. As noted, the numerous inventive aspects described herein may be used singly, or in any desired combination. Additionally, in one or more implementations, the enhancements described herein may be provided to work within defined space limitations for existing packages.

Disclosed hereinbelow with reference to FIGS. 2-11B are various approaches and/or enhancements to creating, for instance, a secure volume for accommodating one or more electronic components, such as one or more encryption and/or decryption modules and associated components of, for instance, a communications card or other electronic assembly to be protected.

Figure 2:
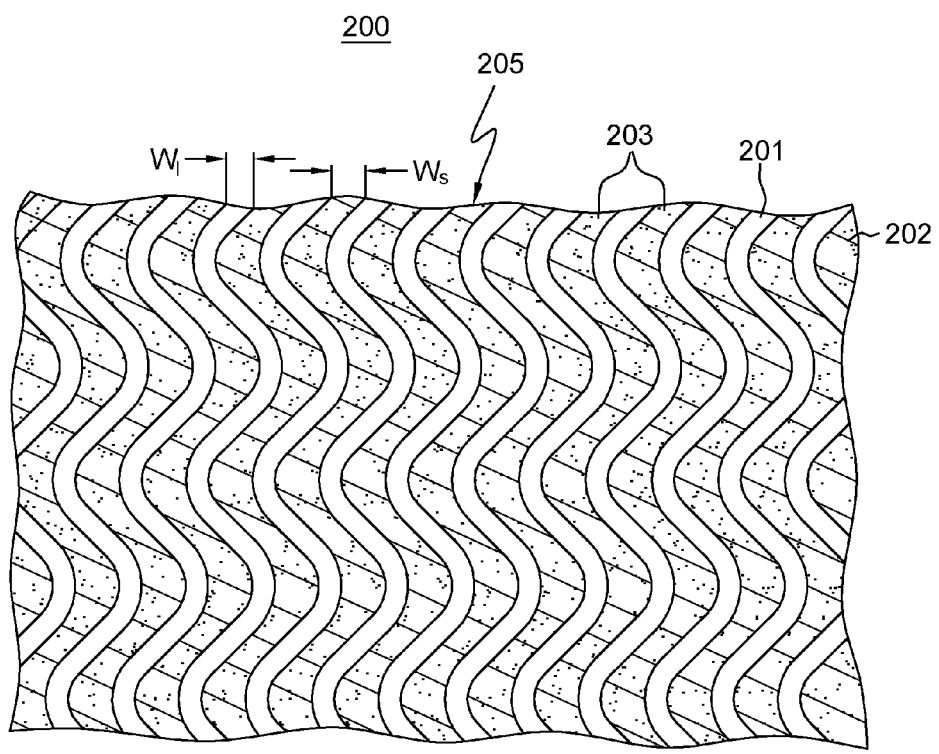
FIG. 2 depicts one embodiment of a tamper-detect sensor with conductive lines forming, at least in part, at least one tamper-detect network, in accordance with one or more aspects of the present invention.

FIG. 2 depicts a portion of one embodiment of a tamper-detection layer 205 (or laser and pierce-respondent layer) of a tamper-detect sensor 200 or security sensor, such as discussed herein. In FIG. 2, tamper-detection layer 205 includes circuit lines or traces 201 provided on one or both opposite sides of a flexible layer 202, which in one or more embodiments, may be a flexible insulating layer or film. FIG. 2 illustrates circuit lines 201 on, for instance, one side of flexible layer 202, with the traces on the opposite side of the film being, for instance, the same pattern, but (in one or more embodiments) offset to lie directly below spaces 203, between circuit lines 201. As described below, the circuit lines on one side of the flexible layer may be of a line width $W_l$ and have a pitch or line-to-line spacing $W_s$ such that piercing of the layer 205 at any point results in damage to at least one of the circuit lines traces 201. In one or more implementations, the circuit lines may be electrically connected in-series or parallel to define one or more conductors which may be electrically connected in a network to an enclosure monitor, which may, in one or more implementations, monitor the resistance of the lines. Detection of an increase, or other change, in resistance, caused by cutting or damaging one of the traces, will cause information within the encryption and/or decryption module to be erased. Providing conductive lines 201 in a pattern, such as a sinusoidal pattern, may advantageously make it more difficult to breach tamper-detection layer 205 without detection. Note, in this regard, that conductive lines 201 could be provided in any desired pattern. For instance, in an alternate implementation, conductive lines 201 could be provided as parallel, straight conductive lines, if desired, and the pattern or orientation of the pattern may vary between sides of a layer, and/or between layers.

As noted, as intrusion technology continues to evolve, anti-intrusion technology needs to continue to improve to stay ahead. In one or more implementations, the above-summarized tamper-detect sensor 200 of FIG. 2 may be disposed over an outer surface of an electronic enclosure, such as an electronic enclosure described above in connection with FIG. 1. Alternatively, as described further herein, the tamper-detect sensor may cover or line an inner surface of an electronic enclosure to provide a secure volume about at least one electronic component to be protected. Still further, the tamper-detect sensor, or more particularly, the tamper-detect circuit(s) of the sensor, could be embedded within a multilayer circuit board described below.

In one or more aspects, disclosed herein is a tamper-detect sensor 200 with circuit lines 201 having reduced line widths $W_l$ of, for instance, 200 μm, or less, such as less than or equal to 100 μm, or even more particularly, in the range of 30-70 μm. This is contrasted with conventional trace widths, which are typically on the order of 250 μm or larger. Commensurate with reducing the circuit line width $W_l$, line-to-line spacing width $W_s$ 203 is also reduced to less than or equal to 200 μm, such as less than or equal to 100 μm, or for instance, in a range of 30-70 μm. Advantageously, by reducing the line width $W_l$ and line-to-line spacing $W_s$ of circuit lines 201 within tamper-detect sensor 200, the circuit line width and pitch is on the same order of magnitude as the smallest intrusion instruments currently available, and therefore, any intrusion attempt will necessarily remove a sufficient amount of a circuit line(s) to cause resistance to change, and thereby the tamper intrusion to be detected. Note that, by making the circuit line width of the smaller dimensions disclosed herein, any cutting or damage to the smaller-dimensioned circuit line will also be more likely to be detected, that is, due to a greater change in resistance. For instance, if an intrusion attempt cuts a 100 μm width line, it is more likely to reduce the line width sufficiently to detect the intrusion by a change in resistance. A change in a narrower line width is more likely to result in a detectable change in resistance, compared with, for instance, a 50% reduction in a more conventional line width of 350 μm to, for instance, 175 μm. The smaller the conductive circuit line width becomes, the more likely that a tampering of that line will be detected.

Note also that a variety of materials may advantageously be employed to form the circuit lines when implemented using resistance monitoring. For instance, the circuit lines may be formed of a conductive ink (such as a carbon-loaded conductive ink) printed onto one or both opposite sides of one or more of the flexible layers 202 in a stack of such layers. Alternatively, a metal or metal alloy could be used to form the circuit lines, such as copper, silver, intrinsically conductive polymers, carbon ink, or nickel-phosphorus (NiP), such as Omega-Ply®, offered by Omega Technologies, Inc. of Culver City, Calif. (USA), or nickel-chrome, such as Ticer™ offered by Ticer Technologies, Chandler, Ariz. (USA). Note that the process employed to form the fine circuit lines or traces on the order described herein is dependent, in part, on the choice of material used for the circuit lines. For instance, if copper circuit lines are being fabricated, then additive processing, such as plating up copper traces, or subtractive processing, such as etching away unwanted copper between trace lines, may be employed. By way of further example, if conductive ink is employed as the circuit line material, fine circuit lines on the order disclosed herein can be achieved by focusing on the rheological properties of the conductive ink formulation. Further, rather than simple pneumatics of pushing conductive ink through an aperture in a stencil with a squeegee, the screen emulsion may be characterized as very thin (for instance, 10 to 30 μm), and a squeegee angle may be used such that the ink is sheared to achieve conductive ink breakaway rather than pumping the conductive ink through the screen apertures. Note that the screen for fine line width printing such as described herein may have the following characteristics in one specific embodiment: a fine polyester thread for both warp and weave on the order of 34-48 micrometers; a thread count between 250-320 threads per inch; a mesh thickness of, for instance, 53-81 micrometers; an open area between threads that is at least 1.5× to 2.0× the conductive ink particle size; and to maintain dimensional stability of the print, the screen snap-off is kept to a minimum due the screen strain during squeegee passage.

In a further aspect, the flexible layer 202 itself may be further reduced in thickness from a typical polyester layer by selecting a crystalline polymer to form the flexible layer or substrate. By way of example, the crystalline polymer could comprise polyvinylidene difluoride (PVDF), or Kapton, or other crystalline polymer material. Advantageously, use of a crystalline polymer as the substrate film may reduce thickness of the flexible layer 202 to, for instance, 50 micrometers thick from a more conventional amorphous polyester layer of, for instance, 125-150 micrometers. A crystalline polymer can be made much thinner, while still maintaining structural integrity of the flexible substrate, which advantageously allows for far more folding, and greater reliability of the sensor after folding. Note that the radius of any fold or curvature of the sensor is necessarily constrained by the thickness of the layers comprising the sensor. Thus, by reducing the flexible layer thickness to, for instance, 50 micrometers, then in a four tamper-detection layer stack, the stack thickness can be reduced from, for instance, 500 micrometers in the case of a typical polyester film, to 250 micrometers or less with the use of crystalline polymer films.

Figure 3A:
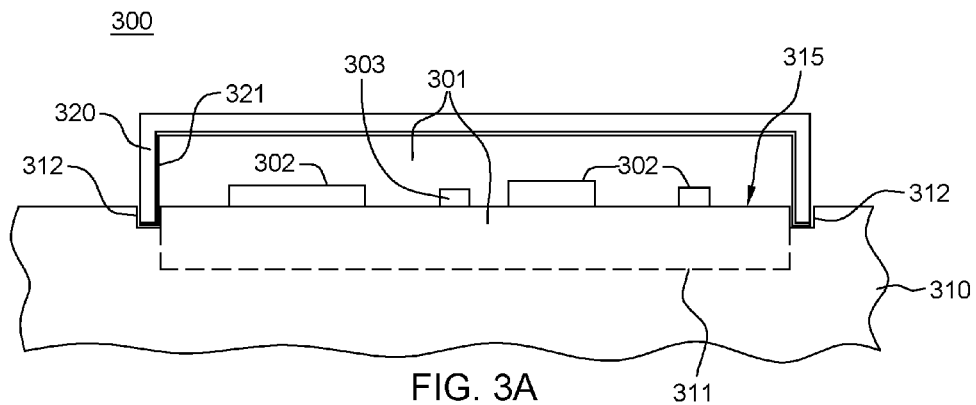
FIG. 3A is a cross-sectional elevational view of another embodiment of a tamper-proof electronic package, or tamper-respondent assembly, which includes (in part) an enclosure, and a multilayer circuit board with an embedded tamper-detect sensor, in accordance with one or more aspects of the present invention.
Figure 3B:
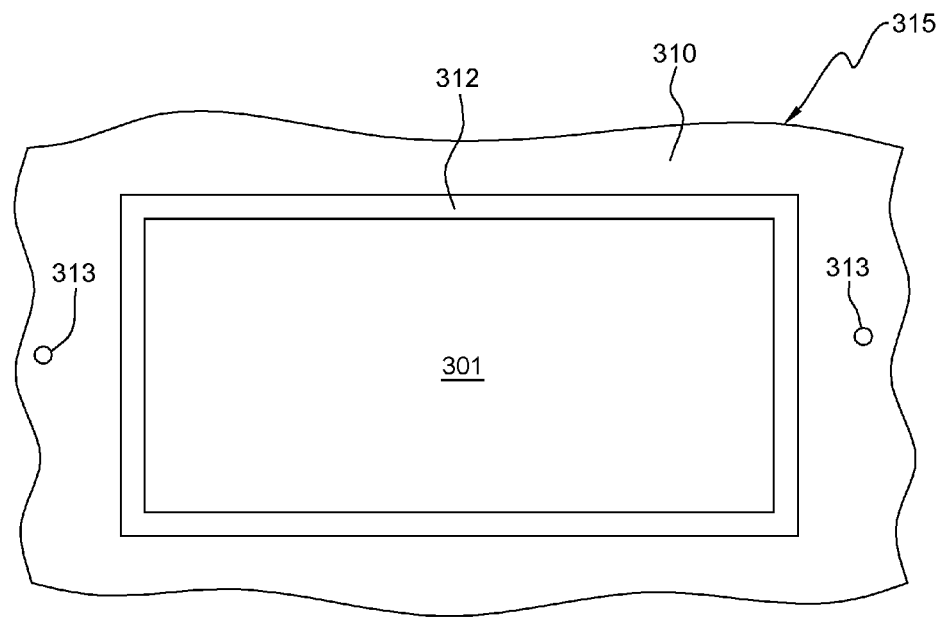
FIG. 3B is a top plan view of the multilayer circuit board of FIG. 3A, depicting one embodiment of the secure volume defined, in part, within the multilayer circuit board, in accordance with one or more aspects of the present invention.

FIGS. 3A & 3B depict one embodiment of a tamper-proof electronic package 300, or tamper-respondent assembly, which comprises one or more electronic components, such as a circuit 315 and/or electronic devices (or elements) 302 to be protected, in accordance with one or more further aspects of the present invention.

Referring collectively to FIGS. 3A & 3B, circuit 315 resides on or is embedded within a multilayer circuit board 310, which also has an embedded tamper-detect sensor 311 that facilitates defining, in part, a secure volume 301 associated with multilayer circuit board 310 that (in one or more embodiments) extends into multilayer circuit board 310. In particular, in the embodiment of FIGS. 3A & 3B, secure volume 301 may exist partially within multilayer circuit board 310, and partially above multilayer circuit board 310. One or more electronic devices 302 are mounted to multilayer circuit board 310 within secure volume 301 and may include, for instance, one or more encryption modules and/or decryption modules, and/or associated components, to be protected within the tamper-proof electronic package. In one or more implementations, the one or more electronic components to be protected may include, for instance, a secure communications card of a computer system.

Tamper-proof electronic package 300 further includes an enclosure 320, such as a pedestal-type enclosure, mounted to multilayer circuit board 310 within, for instance, a continuous groove (or trench) 312 formed within an upper surface of multilayer circuit board 310, and secured to the multilayer circuit board 310 via, for instance, a structural adhesive disposed within continuous groove 312. In one or more embodiments, enclosure 320 may include a thermally conductive material and operate as a heat sink for facilitating cooling of the one or more electronic components 302 within the secure volume. A security mesh or tamper-detect sensor 321 may be associated with enclosure 320, for example, wrapping around the inner surface of enclosure 320, to facilitate defining, in combination with tamper-detect sensor 311 embedded within multilayer circuit board 310, secure volume 301. In one or more implementations, tamper-detect sensor 321 may extend down into continuous groove 312 in multilayer circuit board 310 and may, for instance, even wrap partially or fully around the lower edge of enclosure 320 within continuous groove 312 to provide enhanced tamper detection where enclosure 320 couples to multilayer circuit board 310. In one or more implementations, enclosure 320 may be securely affixed to multilayer circuit board 310 using, for instance, a bonding material such as an epoxy or other adhesive.

Briefly described, tamper-detect sensor 321 may include, in one or more examples, one or more tamper-detection layers which include circuit lines or traces provided on one or both sides of a flexible layer, which in one or more implementations, may be a flexible insulating layer or film. The circuit lines on one or both sides of the flexible layer may be of a line width and have a pitch or line-to-line spacing such that piercing of the layer at any point results in damage to one or more of the circuit lines or traces. In one or more implementations, the circuit lines may define one or more conductors which may be electrically connected in a network to an enclosure monitor or detector 303, which monitors, for instance, resistance on the lines, or as described below, in the case of conductors, may monitor for a nonlinearity, or non-linear conductivity change, on the conductive lines. Detection of a change in resistance or a nonlinearity caused by cutting or damaging one or more of the lines, will cause information within the secure volume to be automatically erased. The conductive lines of the tamper-detect sensor may be in any desired pattern, such as a sinusoidal pattern, to make it more difficult to breach the tamper-detection layer without detection.

For resistive monitoring, a variety of materials may be employed to form the circuit lines. For instance, the circuit lines may be formed of a metal or metal alloy, such as copper, or silver, or could be formed, for example, of an intrinsically-conductive polymer, carbon ink, or nickel phosphorous (NiP), or Omega-Ply®, offered by Omega Technologies, Inc., of Culver City, Calif. (USA), or Ticer™, offered by Ticer Technologies, Chandler, Ariz. (USA). The process employed to form the fine circuit lines or traces is dependent, in part, on the choice of materials used for the circuit lines. For instance, if copper circuit lines are fabricated, then additive processing, such as plating of copper traces, or subtractive processing, such as etching away unwanted copper between trace lines, may be employed.

As noted, in one or more implementations, the circuit lines of the tamper-detect sensor(s) lining the inner surface(s) of enclosure 320, or even printed directly onto one or more layers formed over the inner surface of enclosure 320, may be connected to define one or more detect networks.

If a flexible layer is used over the inner surface of enclosure 320, then the flexible layer may be formed of a crystalline polymer material. For instance, the crystalline polymer could comprise polyvinylidene difluoride (PVDF), or Kapton, or other crystalline polymer material. Advantageously, a crystalline polymer may be made much thinner, while still maintaining structural integrity of the flexible substrate, which also allows for enhanced folding, and greater reliability of the sensor after folding.

As depicted in FIG. 3B, one or more external circuit connection vias 313 may be provided within multilayer circuit board 310 for electrically connecting to the one or more electronic components within secure volume 301. These one or more external circuit connection vias 313 may electrically connect to one or more external signal lines or planes (not shown) embedded within multilayer circuit board 310 and extending, for instance, into a secure base region of (or below) secure volume 301, as explained further below. Electrical connections to and from secure volume 301 may be provided by coupling to such external signal lines or planes within the multilayer circuit board 310.

As noted, secure volume 301 may be sized to house one or more electronic components to be protected, and may be constructed to extend into multilayer circuit board 310. In one or more implementations, multilayer circuit board 310 includes electrical interconnect within the secure volume 301 defined in the board, for instance, for electrically connecting one or more tamper-detection layers of the embedded tamper-detect sensor 311 to associated monitor circuitry also disposed within secure volume 301, along with, for instance, one or more daughter cards, such as memory DIMMs, PCIe cards, processor cards, etc.

Note that the packaging embodiment depicted in FIGS. 3A & 3B is presented by way of example only. Other configurations of enclosure 320, or multilayer circuit board 310 may be employed, and/or other approaches to coupling enclosure 320 and multilayer circuit board 310 may be used. For instance, in one or more alternate implementations, enclosure 320 may be securely affixed to an upper surface of multilayer circuit board 310 (without a continuous groove) using, for instance, a structural bonding material such as an epoxy or other adhesive.

Figure 4:
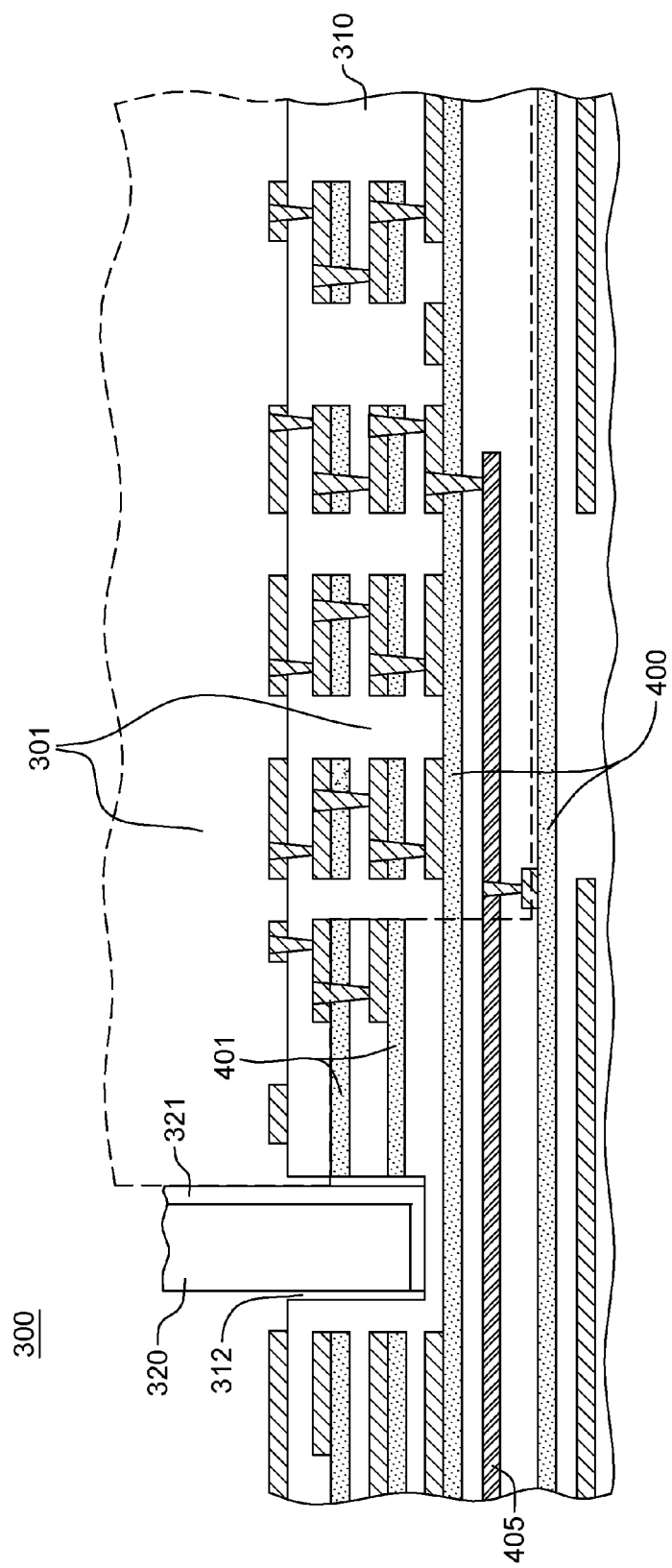
FIG. 4 is a partial cross-sectional elevational view of a more detailed embodiment of the tamper-respondent assembly of FIGS. 3A & 3B comprising (in part) an enclosure and a multilayer circuit board with embedded tamper-detect sensor, in accordance with one or more aspects of the present invention.

By way of further example, FIG. 4 depicts a partial cross-sectional elevational view of a more detailed embodiment of tamper-proof electronic package 300, and in particular, of multilayer circuit board 310, to which enclosure 320 is secured. In this configuration, the embedded tamper-detect sensor includes multiple tamper-detection layers including, by way of example, at least one tamper-detection mat (or base) layer 400, and at least one tamper-detection frame 401. In the example depicted, two tamper-detection mat layers 400 and two tamper-detection frames 401 are illustrated, by way of example only. The lower-most tamper-detection mat layer 400 may be a continuous sense or detect layer extending completely below the secure volume being defined within and/or above multilayer circuit board 310. One or both tamper-detection mat layers 400 below secure volume 301 may be partitioned into multiple circuit zones. Within each tamper-detection mat layer, or more particularly, within each circuit zone of each tamper-detection mat layer, multiple circuits or conductive traces may be provided in any desired configuration. Further, the conductive traces within the tamper-detection layers may be implemented as, for instance, a resistive layer.

As illustrated, one or more external signal lines or planes 405 may enter secure volume 301 between, in one embodiment, two tamper-detection mat layers 400, and then electrically connect upwards into the secure volume 301 through one or more conductive vias, arranged in any desired location and pattern. In the configuration depicted, the one or more tamper-detection frames 401 are disposed at least inside of the area defined by continuous groove 312 accommodating the base of enclosure 320. Together with the tamper-detect sensor(s) 321 associated with enclosure 320, tamper-detection frames 401, and tamper-detection mat layers 400, define secure volume 301, which may extend, in part, into multilayer circuit board 310. With secure volume 301 defined, in part, within multilayer circuit board 310, the external signal line(s) 405 may be securely electrically connected to, for instance, the one or more electronic components mounted to, or of, multilayer circuit board 310 within secure volume 301. In addition, secure volume 301 may accommodate electrical interconnection of the conductive traces of the multiple tamper-detection layers 400, 401, for instance, via appropriate monitor circuitry.

Added security may be provided by extending tamper-detection mat layers 400 (and if desired, tamper-detection frames 401) outward past the periphery of enclosure 320. In this manner, a line of attack may be made more difficult at the interface between enclosure 320 and multilayer circuit board 310 since the attack would need to clear, for instance, tamper-detection mat layers 400, the enclosure 320, as well as the tamper-detection frames 401 of the embedded tamper-detect sensor.

Numerous variations on multilayer circuit board 310 of FIGS. 3A-4 are possible. For instance, in one embodiment, the embedded tamper-detect sensor may include one or more tamper-detection mat layers 400 and one or more tamper-detection frames 401, such as described above, and a tri-plate structure comprising one or more external signal lines or layers sandwiched between an upper ground plane and a lower ground plane. In this configuration, high-speed transfer of signals to and from the secure volume, and in particular, to and from the one or more electronic components resident within the secure volume, would be facilitated.

Note also that, once the secure volume is defined in part within multilayer circuit board 310, conductive vias within the secure volume between layers of multilayer circuit board 310 may be either aligned, or offset, as desired, dependent upon the implementation. Alignment of conductive vias may facilitate, for instance, providing a shortest connection path, while offsetting conductive vias between layers may further enhance security of the tamper-proof electronic package by making an attack into the secure volume through or around one or more tamper-detection layers of the multiple tamper-detection layers more difficult.

The tamper-detection layers of the embedded tamper-detect sensor formed within the multilayer circuit board of the electronic circuit or electronic package may include multiple conductive traces or lines formed between, for instance, respective sets of input and output contacts or vias at the trace termination points. Any pattern and any number of conductive traces or circuits may be employed in defining a tamper-detection layer or a tamper-detection circuit zone within a tamper-detection layer. For instance, 4, 6, 8, etc., conductive traces may be formed in parallel (or otherwise) within a given tamper-detection layer or circuit zone between the respective sets of input and output contacts to those conductive traces.

Figure 5:
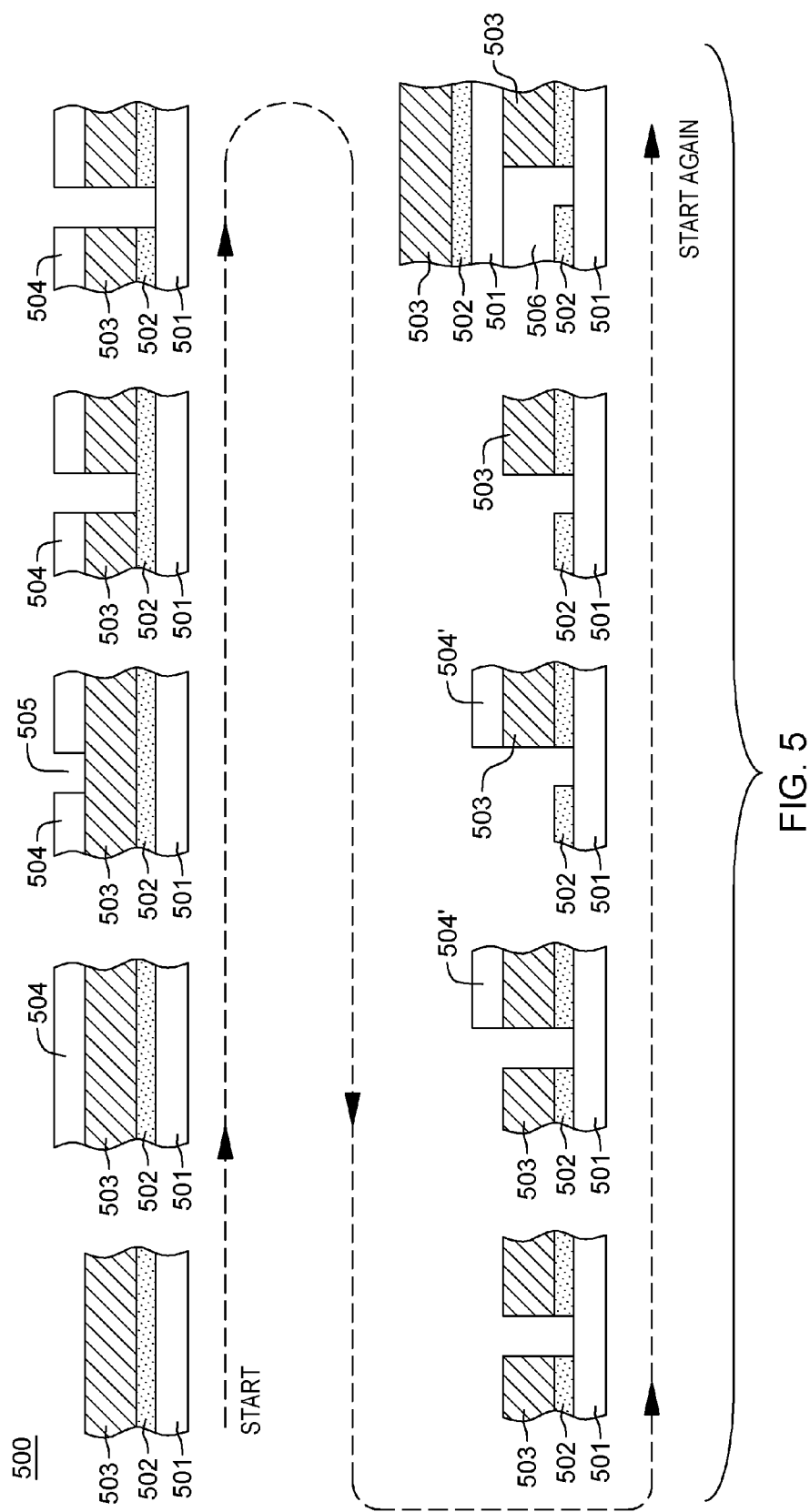
FIG. 5 depicts one embodiment of a process of fabricating a multilayer circuit board with an embedded tamper-detect sensor, in accordance with one or more aspects of the present invention.

In one or more implementations, the multilayer circuit board may be a multilayer wiring board or printed circuit board formed, for instance, by building up the multiple layers of the board. FIG. 5 illustrates one embodiment for forming and patterning a tamper-detection layer within such a multilayer circuit board.

As illustrated in FIG. 5, in one or more implementations, a tamper-detection layer, such as a tamper-detection mat layer or a tamper-detection frame disclosed herein, may be formed by providing a material stack comprising, at least in part, a structural layer 501, such as a pre-preg (or pre-impregnated) material layer, a trace material layer 502 for use in defining the desired trace patterns, and an overlying conductive material layer 503, to be patterned to define conductive contacts or vias electrically connecting to the pattern of traces being formed within the trace material layer 502, for instance, at trace terminal points. In one or more implementations, the trace material layer 502 may comprise nickel phosphorous (NiP), and the overlying conductive layer 503 may comprise copper. Note that these materials are identified by way of example only, and that other trace and/or conductive materials may be used within the build-up 500.

A first photoresist 504 is provided over build-up 500, and patterned with one or more openings 505, through which the overlying conductive layer 503 may be etched. Depending on the materials employed, and the etch processes used, a second etch process may be desired to remove portions of trace material layer 502 to define the conductive traces of the subject tamper-detection layer. First photoresist 504 may then be removed, and a second photoresist 504' is provided over the conductive layer 503 features to remain, such as the input and output contacts. Exposed portions of conductive layer 503 are then etched, and the second photoresist 504' may be removed, with any opening in the layer being filled, for instance, with an adhesive (or pre-preg) 506 and a next build-up layer is provided, as shown. Note that in this implementation, most of overlying conductive layer 503 is etched away, with only the conductive contacts or vias remaining where desired, for instance, at the terminal points of the traces formed within the layer by the patterning of the trace material layer 502. Note that any of a variety of materials may be employed to form the conductive lines or traces within a tamper-detection layer. Nickel-phosphorous (NiP) is particularly advantageous as a material since it is resistant to contact by solder, or use of a conductive adhesive to bond to it, making it harder to bridge from one circuit or trace to the next during an attempt to penetrate into the protected secure volume of the electronic circuit. Other materials which could be employed include OhmegaPly®, offered by Ohmega Technologies, Inc., of Culver City, Calif. (USA), or Ticer™, offered by Ticer Technologies of Chandler, Ariz. (USA).

The trace lines or circuits within the tamper-detection layers, and in particular, the tamper-detection circuit zones, of the embedded tamper-detect sensor, along with the tamper detector monitoring the enclosure, may be electrically connected to detect or compare circuitry provided, for instance, within secure volume 301 (FIG. 3A) of the tamper-proof electronic package. The detect circuitry may include various bridges or compare circuits, and conventional printed wiring board electrical interconnect inside secure volume 301 (FIG. 3A), for instance, located within the secure volume defined by the tamper-detection frames 401 (FIG. 4), and the tamper-detection mat layers 400 (FIG. 4).

Note that advantageously, different tamper-detection circuit zones on different tamper-detection layers may be electrically interconnected into, for instance, the same detect circuitry. Thus, any of a large number of interconnect configurations may be possible. For instance, if each of two tamper-detection mat layers contains 30 tamper-detection circuit zones, and each of two tamper-detection frames contains 4 tamper-detection circuit zones, then, for instance, the resultant 68 tamper-detection circuit zones may be connected in any configuration within the secure volume to create the desired arrangement of circuit networks within the secure volume being monitored for changes in resistance or tampering. Note in this regard, that the power supply or battery for the tamper-detect sensor may be located internal or external to the secure volume, with the sensor being configured to trip and destroy any protected or critical data if the power supply or battery is tampered with.

Figure 6:
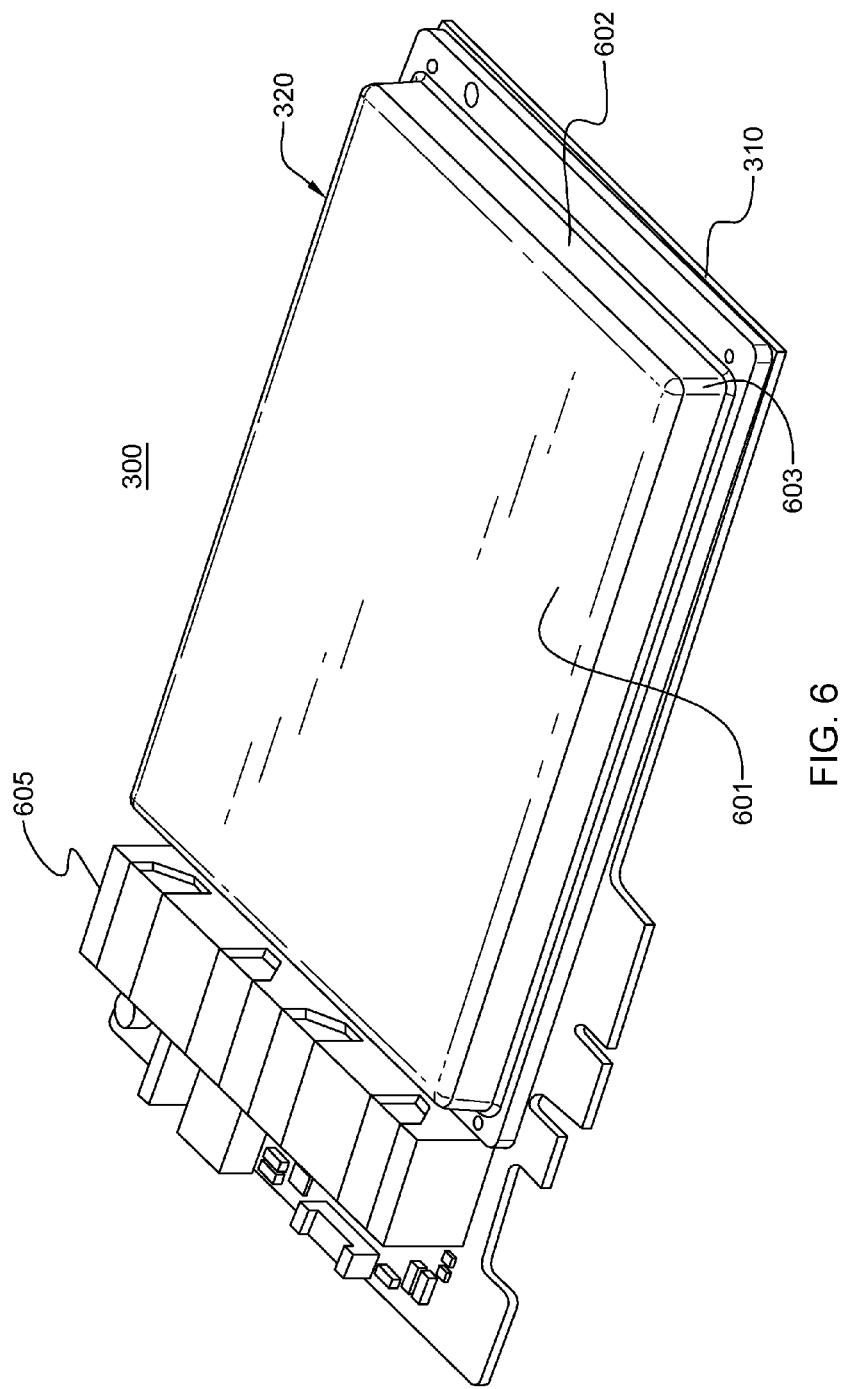
FIG. 6 is an isometric view of one embodiment of a tamper-respondent assembly, in accordance with one or more aspects of the present invention.

By way of further example, an isometric view of one embodiment of a tamper-proof electronic package 300 is depicted in FIG. 6, wherein an enclosure 320 is shown sealed to multilayer circuit board 310 to define a secure volume about one or more electronic components, as described herein. In one or more embodiments, enclosure 320 may be formed of a thermally conductive material, and include a main surface 601 and sidewall(s) 602 which include sidewall corners 603. An inner surface of enclosure 320 would include an inner main surface, and an inner sidewall surface corresponding to main surface 601 and sidewall(s) 602, respectively, with the inner main surface and inner sidewall surfaces being covered, at least in part, by one or more tamper-detect sensors, such as described above. A power supply 605 or battery for the tamper-detect sensor may be located, as depicted in this embodiment, external to the secure volume, with the tamper detector being configured to trip and destroy any protected or critical data if the power supply or battery is tampered with. Enclosure 320 may be adhered or mechanically affixed to multilayer circuit board 310, which as noted above, may include its own embedded tamper-detect sensor(s).

Figure 7A:
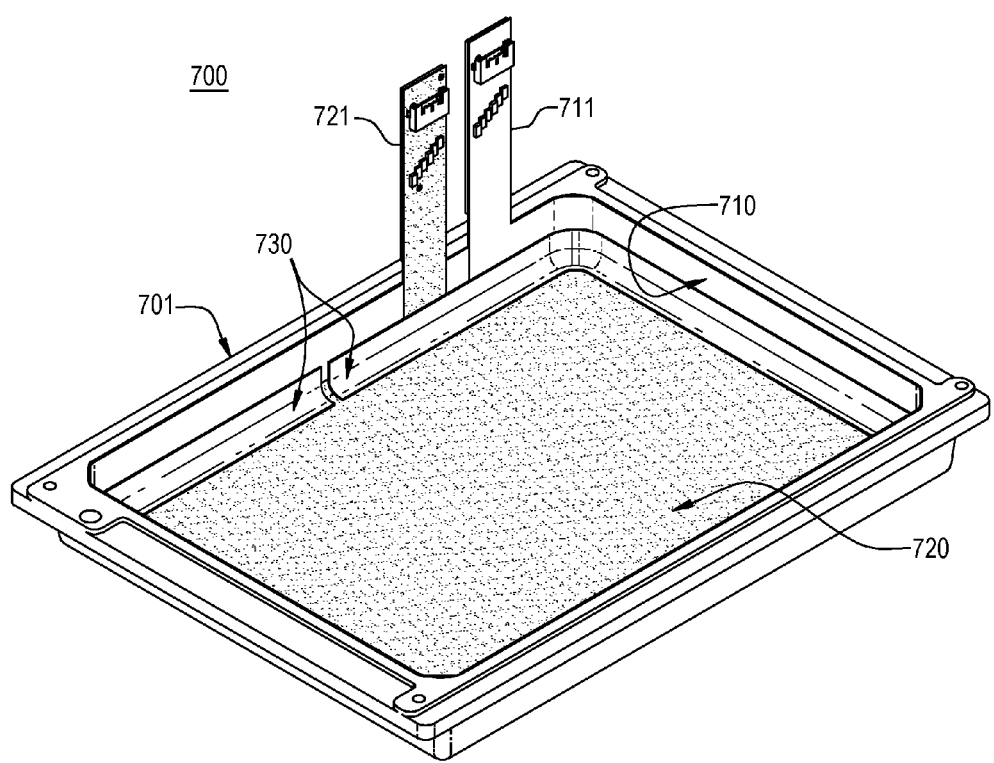
FIG. 7A depicts an underside, perspective view of one embodiment of an electronic enclosure and tamper-detect sensor subassembly of a tamper-respondent assembly, in accordance with one or more aspects of the present invention.
Figure 7B:
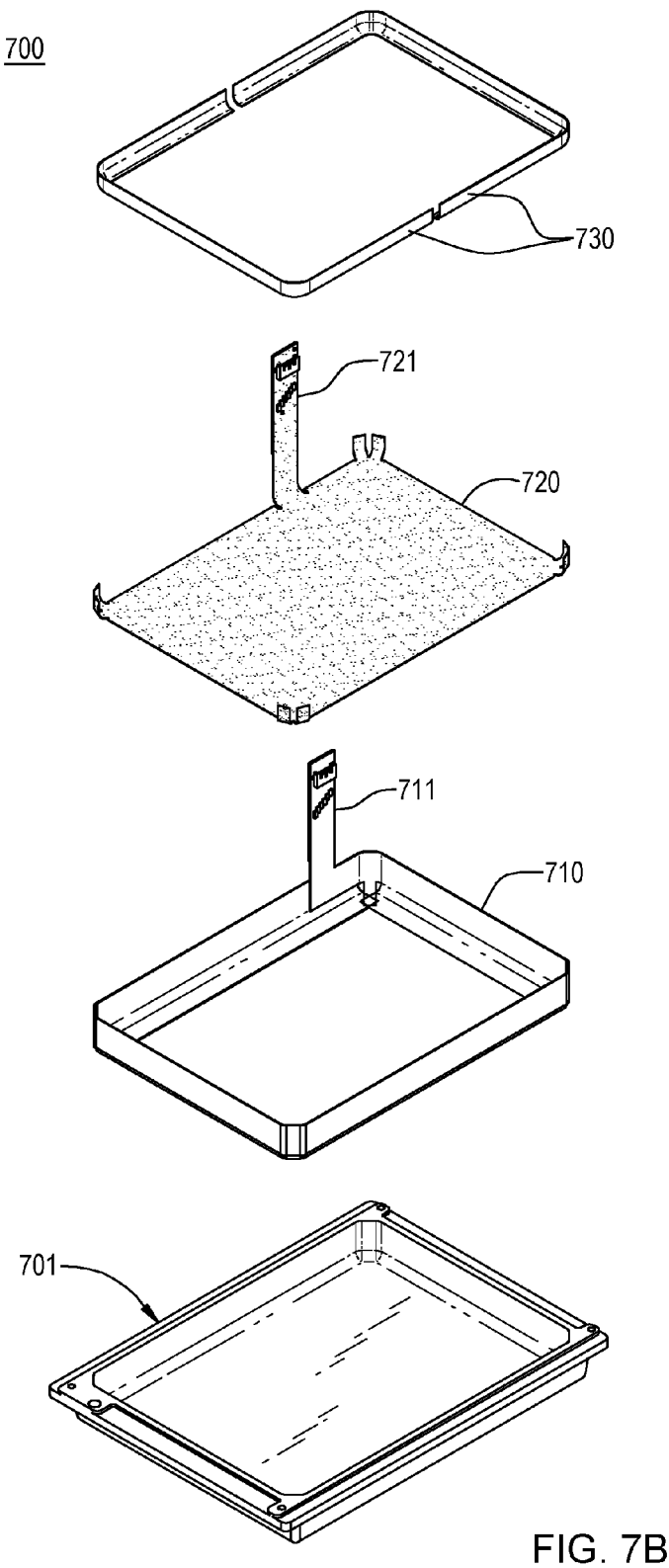
FIG. 7B depicts an exploded view of the subassembly of FIG. 7A, in accordance with one or more aspects of the present invention.

FIGS. 7A & 7B depict underside, isometric views of an embodiment of a tamper-respondent assembly 700 employing an electronic enclosure 701. Referring collectively to FIGS. 7A & 7B, in one or more implementations, tamper-respondent assembly 700 includes an electronic enclosure 701 which, as noted, is to enclose, at least in part, one or more electronic components or an electronic assembly to be protected. Electronic enclosure 701 may include an inner main surface, and an inner sidewall surface including at least one inner-sidewall corner, such as described above. Further, tamper-respondent assembly 700 includes a tamper-detection electronic circuit structure which includes at least one tamper-detect sensor mounted to and covering, at least in part, the inner surface(s) of electronic enclosure 701. As explained further below, the tamper-detect sensor(s) is configured to facilitate good contact, and good adhesion, of the sensor to the inner surfaces of the enclosure, such as, for instance, the one or more inner-sidewall corners of the electronic enclosure 701, to provide secure coverage of the tamper-detect sensor(s) over the inner surface(s) of the electronic enclosure.

As illustrated, in one or more implementations, the tamper-respondent electronic circuit structure associated with electronic enclosure 701 may include an inner-sidewall tamper-detect sensor 710 and an inner main surface tamper-detect sensor 720, along with a security band 730. In the illustrated example, inner-sidewall tamper-detect sensor 710 may be formed with an integrated flex ribbon cable or extension 711 to facilitate electrical connection of the at least one detect network within inner-sidewall tamper-detect sensor 710 to appropriate monitor circuitry (not shown) disposed within, for instance, the secure volume defined, at least in part, by the tamper-respondent assembly of FIGS. 7A & 7B. Similarly, inner main surface tamper-detect sensor 720 may be configured with an integrated flex ribbon cable or extension 721 to facilitate electrical connection of inner main surface tamper-detect sensor 720 to the monitor circuitry, as well. A bonding agent (not shown), such as a thermoset adhesive, may be employed to adhere inner-sidewall tamper-detect sensor 720 to inner sidewall surface and to inner-sidewall corners. A similar adhesive could be used to adhere inner main surface tamper-detect sensor 720 to the inner main surface and to inner-sidewall tamper-detect sensor 710 where the sensors overlap. Security band 730 may further be adhesively secured over the overlap between inner main surface tamper-detect sensor 720 and inner-sidewall tamper-detect sensor 710 covering, in one or more implementations, the transition region between the inner sidewall surface and the inner main surface around the inner perimeter of electronics enclosure 701.

Note that, in the example provided in FIGS. 7A & 7B, inner-sidewall tamper-detect sensor 710 and inner main surface tamper-detect sensor 720 are discrete tamper-detect sensors that overlap, at least in part, and facilitate defining a secure volume about the at least one electronic component to be protected. For instance, the secure volume may be defined by flipping over and securing the illustrated tamper-respondent assembly of FIGS. 7A & 7B to a multilayer circuit board with an embedded tamper-detect sensor, such as described above.

A variety of tamper-respondent assembly configurations are disclosed herein which may employ an adhesive in one or more external bond regions on a surface of the tamper-detect sensor(s) to secure, for instance, a tamper-detect sensor in an operative position within the tamper-respondent assembly. By way of example, the adhesive may be employed to maintain a particular configuration of the tamper-detect sensor about an electronic enclosure, or to bond two or more tamper-detect sensors together in a multi-sensor configuration, or to position a tamper-detect sensor relative to an electronic enclosure of a tamper-respondent assembly, such as over an inner surface of an electronic enclosure. These external bond regions could be susceptible to attack against the adhesive.

Therefore, by way of further enhancement, increased sensitivity to a tamper event may be provided by fabricating the tamper-respondent assembly to include conductive traces positioned and fabricated to have increased mechanical and/or chemical fragility or susceptibility to damage from a tamper event, and in particular to a tamper event at an external bond or overlap region of the sensor. For instance, one or more conductive traces may be exposed within a bond region(s) of one or more tamper-detect sensors, and an adhesive provided contacting the conductive trace(s) within the bond region(s) of the tamper-detect sensor(s). By directly contacting the adhesive to the conductive traces, any attempt to mechanically and/or chemically tamper with the adhesive, to facilitate gaining access to the secure volume within the tamper-respondent assembly, is more likely to damage one or more conductive traces, and thus be detected. Note in this regard, that by forming the conductive traces of a chemically compromisable or dissolvable conductive material during a chemical attack on the adhesive, then the conductive traces will likely be damaged during the attack on the adhesive. In at least this manner, the exposed conductive traces may provide increased fragility or susceptibility to mechanical and/or chemical attack at the external bond region(s).

As noted, the at least one external bond region may be a region of the tamper-detect sensor(s) where the sensor adheres to another surface, such as the surface of a rigid structure of the tamper-respondent assembly, or the surface of another tamper-detect sensor, in a multi-tamper-detect sensor embodiment, or even to another region of the same tamper-detect sensor. In each of these examples, one or more conductive traces could be provided to form, for instance, an outer tamper-detect network that is exposed, at least in part, on a surface of the one or more tamper-detect sensors within the bond region(s) of the sensor(s).

In one or more embodiments, these one or more conductive traces may be distinct conductors from the unexposed circuit lines on the flexible layers within the tamper-detect sensor(s). For instance, and as noted, conductive traces may be formed of a chemically compromisable or dissolvable material susceptible to damage during a chemical attack of the adhesive within the bond region(s) of the tamper-detect sensor(s) to facilitate detecting the chemical attack, whereas the unexposed circuit lines forming the tamper-detect sensor may be of a different conductive material (and may even be of different line width, and/or line-to-line spacing) to facilitate, for instance, securing the one or more electronic components to be protected against a mechanical tamper event through the sensor. In one or more examples, the circuit lines within the tamper-detect sensor(s) may be smaller and of closer pitch than the conductive traces exposed on the surface of the tamper-detect sensor(s) within the bond region(s). The one or more conductive traces forming the outer tamper-detect network may be placed on the tamper-detect sensor(s) in any location susceptible to a chemical attack, such as where adhesive is employed to bond the tamper-detect sensor to another surface of the tamper-respondent assembly, such as to an electronic enclosure, or to another tamper-detect sensor of the assembly, or even to itself, depending on the implementation.

Figure 8A:
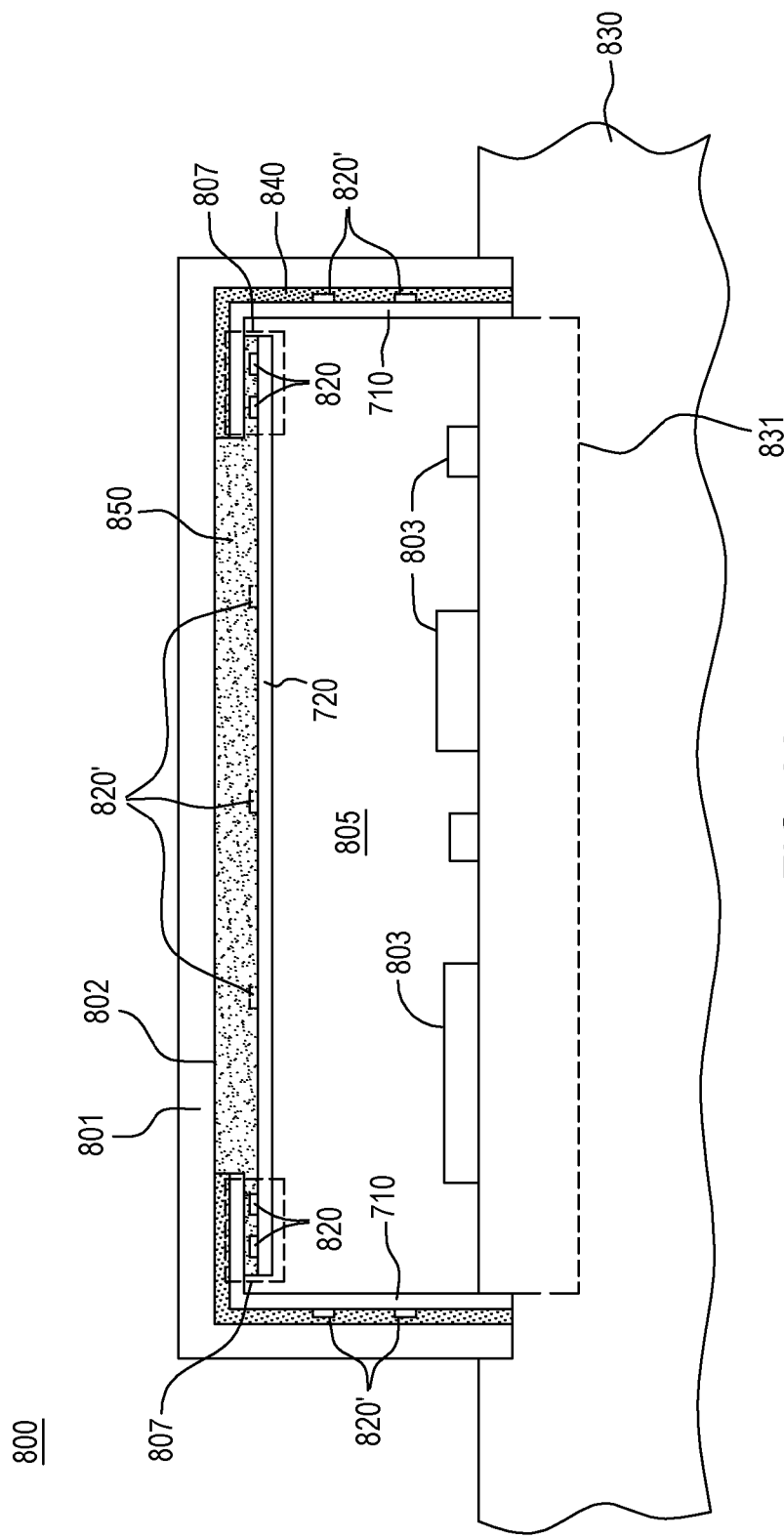
FIG. 8A is a cross-sectional elevational view of another embodiment of a tamper-respondent assembly including first and second tamper-detect sensors secured to an inner surface of an electronic enclosure, in accordance with one or more aspects of the present invention.
Figure 8B:
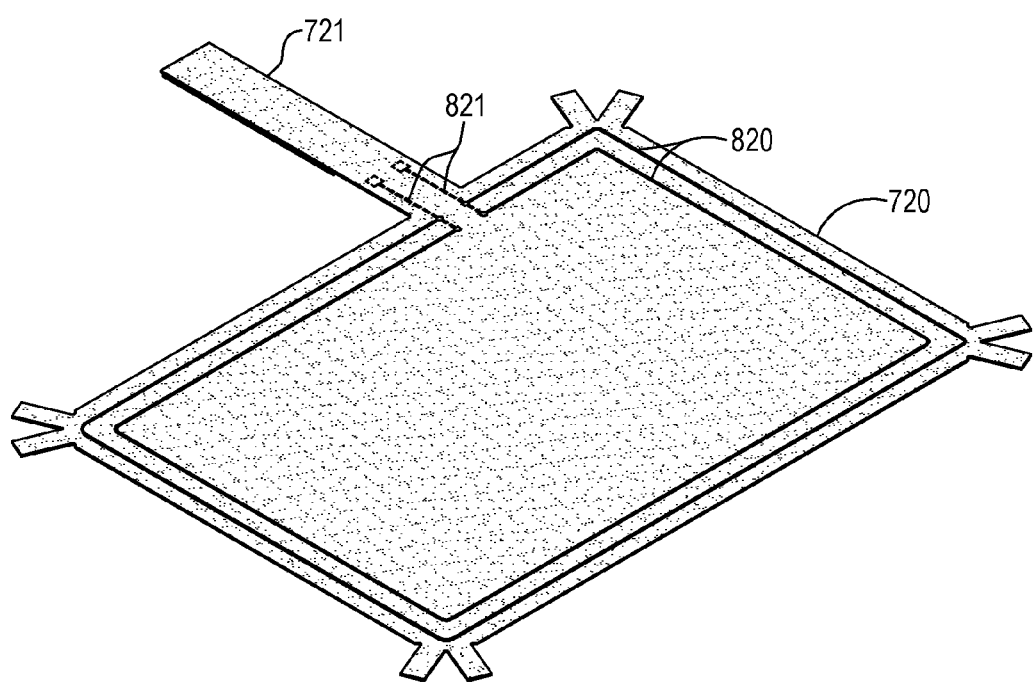
FIG. 8B is an isometric view of one embodiment of an inner-main-surface, tamper-detect sensor with one or more conductive traces in one or more bond regions thereof, in accordance with one or more aspects of the present invention.
Figure 8C:
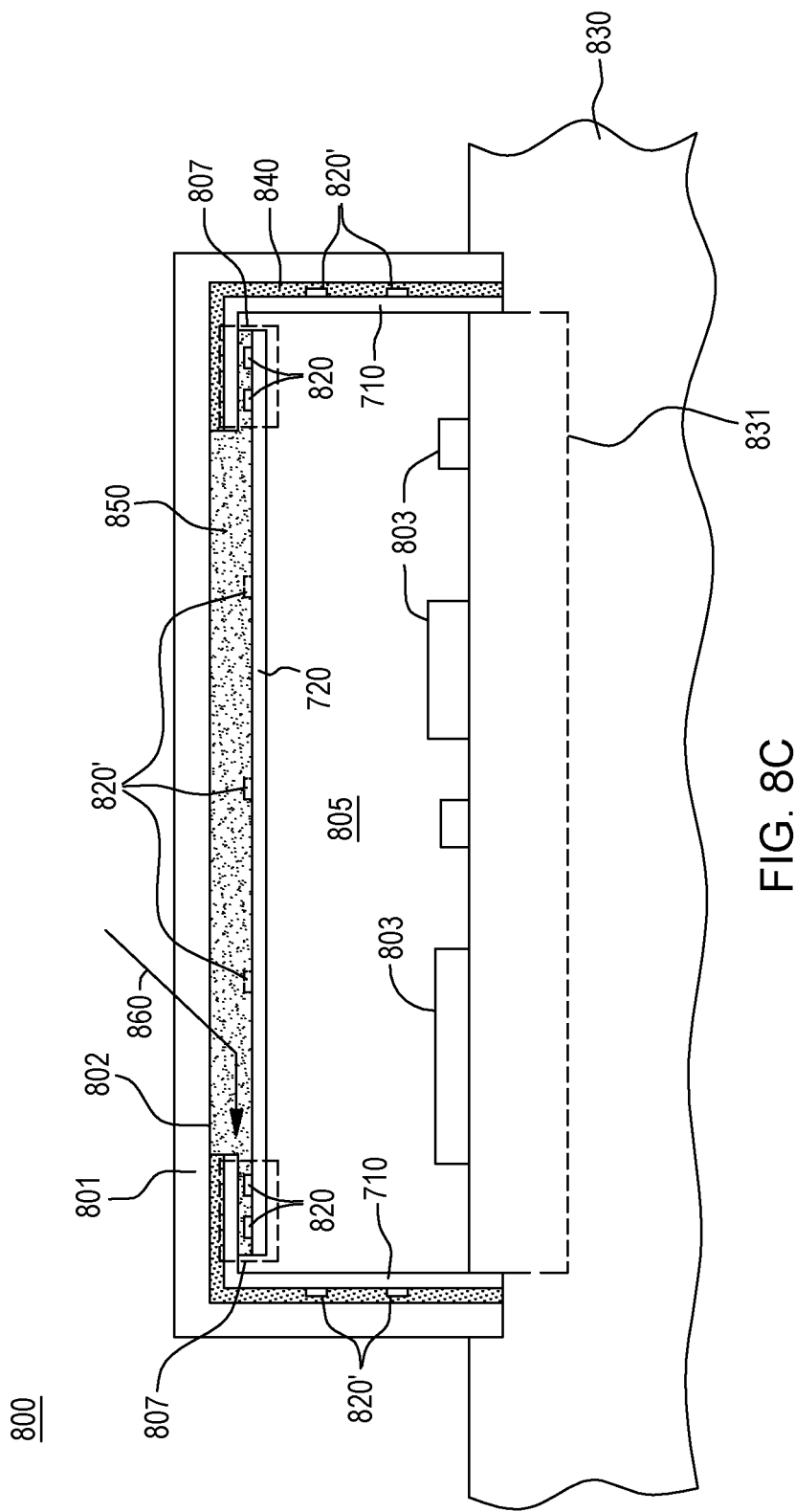
FIG. 8C is a cross-sectional elevational view of the tamper-respondent assembly of FIG. 8A, illustrating an attempted line of attack through the electronic enclosure and adhesive encountering the one or more conductive traces, in accordance with one or more aspects of the present invention.

FIGS. 8A-8C depict one embodiment of a tamper-respondent assembly having one or more tamper-detect sensors with conductive traces positioned and fabricated to facilitate detection of a mechanical and/or chemical attack against an adhesive of the tamper-respondent assembly.

Referring to FIG. 8A, a tamper-respondent assembly 800 is depicted including a structure 801 having a rigid surface 802. By way of example, structure 801 is illustrated as an electronic enclosure or housing surrounding, at least in part, one or more electronic components 803 to be protected. By way of specific example, rigid surface 802 is shown (by example) as an inner surface of the electronic enclosure, such as an inner surface of electronic enclosure 701 described above in connection with FIGS. 7A-7B. The embodiment of FIG. 8A is presented, by way of example only, in connection with the implementation of FIGS. 3A-7B, where one or more tamper-detect sensors are adhered to an inner surface of an electronic enclosure. In this example, conductive traces 820 may be provided between discrete first and second tamper-detect sensors (such as inner-sidewall tamper-detect sensor 710 and inner main surface tamper-detect sensor 720), or alternatively, or additionally, conductive traces 820' may be provided between one or more of the tamper-detect sensors and the inner surface of the enclosure.

Note also that, in one or more other implementations, the conductive traces described herein as susceptible to damage during chemical attack of the adhesive, could be disposed between one or more tamper-detect sensors and an outer surface of a structure, such as an outer surface of an electronic enclosure. In this regard, reference the embodiment of FIG. 1, where one or more tamper-detect sensors of a tamper-respondent electronic circuit structure may be adhered to an outer surface of an electronic enclosure. Still further, the conductive traces forming the outer tamper-detect network might be between the tamper-detect sensor and any rigid structure of an electronic assembly, or cooling apparatus of an electronic assembly to be protected. For instance, the conductive traces disclosed herein could be disposed between one or more tamper-detect sensors and a heat sink, such as a thermal spreader.

As illustrated, in one or more implementations, the tamper-respondent electronic circuit structure of the tamper-respondent assembly 800 may include inner-sidewall tamper-detect sensor 710 and inner main surface tamper-detect sensor 720, each including one or more tamper-detect networks, such as one or more unexposed tamper-detect networks formed by circuit lines on one or more flexible layers, such as described above. The one or more tamper-detect networks are electrically connected to appropriate monitor circuitry (not shown) disposed within, for instance, the secure volume 805 defined by tamper-respondent assembly 800. Note that in this example, inner-sidewall tamper-detect sensor 710 and inner main surface tamper-detect sensor 720 are discrete, first and second tamper-detect sensors that overlap, at least in part, and facilitate defining the secure volume about the at least one electronic component 803 to be protected. For instance, the secure volume may be defined by securing the electronic enclosure to a multilayer circuit board 830 with an embedded tamper-detect sensor 831, such as described above. Note further, in the depicted configuration, inner-sidewall tamper-detect sensor 710 may be bonded via an adhesive 840 to an inner-sidewall surface of the electronic enclosure, wrapping partially around and over, onto the inner main surface of the electronic enclosure, as shown. This allows the overlap region 807 of the inner-sidewall tamper-detect sensor 710 and inner main surface tamper-detect sensor 720 to occur at the flat, inner main surface portion of the structure 801. An adhesive 850 is provided to bond inner main surface tamper-detect sensor 720 to the inner main surface of structure 801, as well as to the inner-sidewall tamper-detect sensor 710 in overlap region(s) 807. Adhesives 840, 850 may be the same or different adhesives. In one or more implementations, adhesives 840, 850 may be a thermoset material, such as a thermally conductive epoxy.

As noted, to provide enhanced tamper-detect protection, one or more conductive traces 820 may be provided exposed, at least in part, on one or more of the tamper-detect sensors 710, 720 of tamper-respondent assembly 800. For instance, one or more conductive traces 820 are illustrated in the overlap region 807 between inner-sidewall tamper-detect sensor 710 and inner main surface tamper-detect sensor 720, by way of example. Additionally, or alternatively, one or more conductive traces 820' could be provided, as part of the same or a different tamper-detect network(s), on a surface of inner-sidewall tamper-detect sensor 710 between inner-sidewall tamper-detect sensor 710 and an inner-sidewall of structure 801, and/or on a surface of inner main surface tamper-detect sensor 720, between inner main surface tamper-detect sensor 720 and rigid surface 802 of structure 801. In one or more implementations, the conductive traces 820, 820' in the bond region(s) are formed of a chemically compromisable or dissolvable conductive material susceptible to wetting or other damage during a chemical attack of the adhesive 840, 850 in direct contact therewith. The damage may result in dissolving one or more portions of the conductive traces, and thus, one or more portions of the associated tamper-detect network(s) defined (at least in part) by the traces and being monitored by the tamper-respondent electronic circuit structure, thereby facilitating detecting the tamper event. Note that the chemically dissolvable conductor used to form the conductive traces may be the same or a different material than the material used to form the unexposed circuit lines defining the one or more tamper-detect networks of the respective tamper-detect sensor.

Stated generally, the conductive traces may be formed of a chemically compromisable conductive material, and may be provided in any bond region external to one or more sensors where, for instance, an adhesive bonds the respective tamper-detect sensor to another surface, such as another surface of the tamper-respondent assembly. By way of example, the chemically dissolvable material used to form the conductive traces may include, at least in part, at least one of carbon, silver, or carbon-silver. For instance, the one or more conductive traces of the respective tamper-detect network(s) may be formed of a carbon-loaded conductive material, silver-loaded conductive material, or carbon-silver-loaded conductive material. Note also that different conductive traces may be in the same or different tamper-detect networks, and that conductive traces may be in the same or a different tamper-detect network than the network(s) defined by the sensor's unexposed circuit lines.

FIG. 8B depicts a modified version of inner main surface tamper-detect sensor 720 described above. As described, inner main surface tamper-detect sensor 720 includes one or more flexible layers having opposite first and second sides, and circuit lines on the flexible layer(s) forming, at least in part, at least one tamper-detect network, such as at least one resistive network, where the circuit lines may be disposed on at least one of the first side or the second side the flexible layer(s). For instance, multiple flexible layers could be provided within a stack, with circuit lines being defined on each side of each flexible layer within the stack, in any desired pattern and in any desired network configuration, to facilitate detection of a mechanical attempt to gain access to the secure volume through the tamper-detect sensor.

In the example of FIG. 8B, multiple conductive traces 820 are also provided about the periphery of inner main surface tamper-detect sensor 720 in an area which aligns with a bond region of the tamper-detect sensor, and in particular, aligns to an overlap region of, for instance, inner-sidewall tamper-detect sensor 710, such as depicted in FIG. 8A. Note in this regard, that two conductive traces 820 are shown by way of example only. One, or more than two conductive traces in any desired pattern could be provided within the bond region(s). Note also that, in the example of FIG. 8A, the bond region includes substantially the entire upper surface of the inner main surface tamper-detect sensor 720, since the inner main surface tamper-detect sensor 720 is either bonded to the inner main rigid surface 802 (FIG. 8A) or to inner-sidewall tamper-detect sensor 710 (FIG. 8A). The conductive traces 820 are illustrated in FIG. 8B in the overlap region 807 (FIG. 8A) between the two tamper-detect sensors of the tamper-respondent assembly shown in FIG. 8A. Note that in this implementation, a tamper-detect network is formed, at least in part, by conductive traces 820, and that this network may further include unexposed circuit lines 821, such as unexposed circuit lines within the tamper-detect sensor 720 itself. That is, a tamper-detect network may include both exposed conductive traces 820 on a surface of the sensor and unexposed circuit lines 821, as desired for a particular application. The unexposed circuit lines may be provided within the tamper-detect sensor to, for instance, complete the tamper-detect network where not needed to be external for tamper-detect purposes. For example, in the implementation of FIG. 8B, the unexposed circuit lines 821 are shown extending within integrated flex ribbon cable or extension 721 of inner main surface tamper-detect sensor 720. The integrated flex ribbon cable or extension 721 would be within the secure volume 805 in the implementation of FIG. 8A to, for instance, facilitate electrical connection of the inner main surface tamper-detect sensor 720 to monitor circuitry within the secure volume. Note further, in one or more other implementations, where the bond region of the tamper-detect sensor includes only a portion of the outer surface of the tamper-detect sensor, that both unexposed circuit lines and exposed conductive traces may be employed in forming one or more tamper-detect networks, with the exposed conductive traces only residing in the bond region to provide the enhanced tamper-detection capability disclosed herein in areas susceptible to mechanical and/or chemical attack of the adhesive.

FIG. 8C illustrates a potential line of attack 860 addressed by the enhanced tamper-respondent assembly of FIGS. 8A & 8B. In particular, line of attack 860 may be attempted through structure 801, into adhesive 850, with the attack involving a chemical attack against the adhesive in order to, for instance, separate inner main surface tamper-detect sensor 720 from inner sidewall tamper-detect sensor 710, and/or from the inner main surface of structure 801. By providing one or more of conductive traces 820, 820' as illustrated, any chemical attack against adhesive 850 will also wet or otherwise damage conductive traces 820, 820', with the damage to the conductive traces facilitating detection of the chemical attack by the monitor circuitry, and thus, initiation of an alarm and/or triggering of an erasure of, for instance, encryption/decryption keys stored within the secure volume.

Figure 9A:
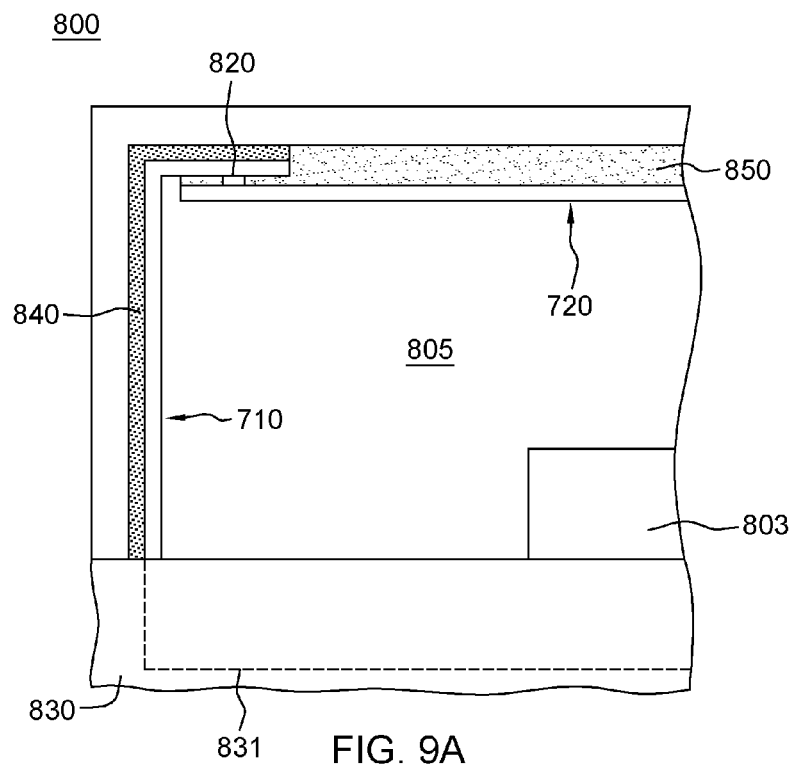
FIG. 9A is an enlarged, cross-sectional elevational view of a further embodiment of a tamper-respondent assembly including first and second tamper-detect sensors secured to an inner surface of an electronic enclosure, in accordance with one or more aspects of the present invention.
Figure 9B:
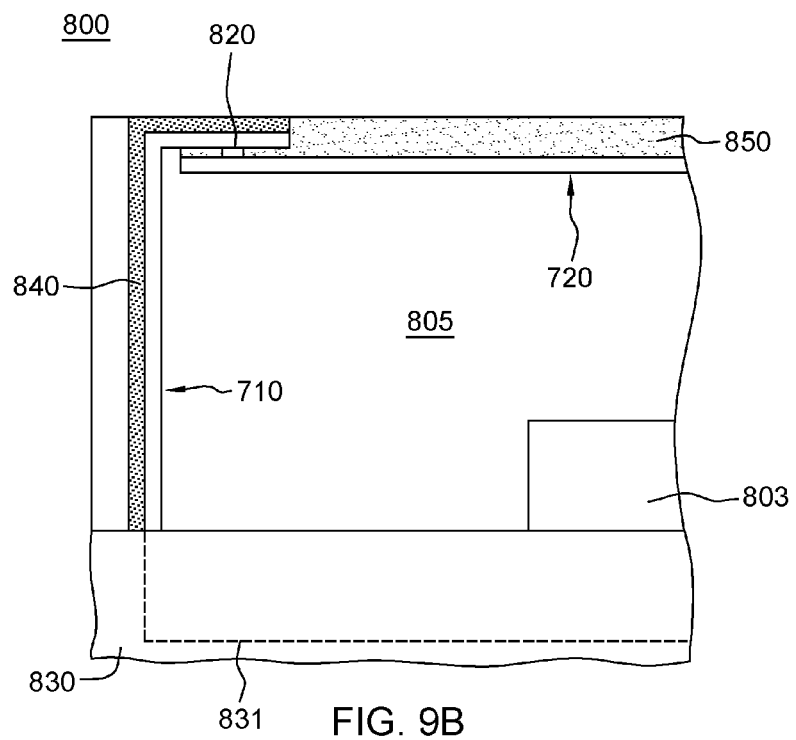
FIG. 9B is a cross-sectional elevational view of the tamper-respondent assembly of FIG. 9A, illustrating an attempted line of attack through the electronic enclosure and the adhesive, again encountering the one or more conductive traces, in accordance with one or more aspects of the present invention.

FIGS. 9A & 9B depict another embodiment of a tamper-respondent assembly including first and second tamper-detect sensors secured to an inner surface of an electronic enclosure, such as described above. In this embodiment, increased sensitivity to a tamper event is provided by including a single conductive trace, positioned and fabricated to have increased mechanical and/or chemical fragility or susceptibility to damage from a tamper event, and in particular, to a tamper event at an external bond or overlap region of the sensor. By directly contacting the adhesive to the conductive trace, an attempt to mechanically and/or chemically tamper with the adhesive, to gain access to the secure volume within the tamper-respondent assembly, is likely to damage the conductive trace, and thus be detected. As noted above, in this manner, the exposed conductive trace provides increased fragility or susceptibility to mechanical and/or chemical attack at the external bond region(s).

Referring collectively to FIGS. 9A & 9B, the external bond region may be a region where a first tamper-detect sensor, such as inner main surface tamper-detect sensor 720, adheres to another surface, such as the surface of a rigid structure of the tamper-respondent assembly, or the surface of another tamper-detect sensor, such as inner-sidewall tamper-detect sensor 710. In this example, a conductive trace 820 is provided at the bond interface between these tamper-detect sensors. As explained above, and as illustrated in FIGS. 9A & 9B, tamper-respondent assembly 800 includes a structure 801, such as an electronic enclosure or housing surrounding, at least in part, one or more electronic components 803 to be protected. Again, the embodiment of FIGS. 9A & 9B is presented, by way of example only. In this example, conductive trace 820 is provided between the discrete first and second tamper-detect sensors (such as inner-sidewall tamper-detect sensor 710 and inner main surface tamper-detect sensor 720), or alternatively, or additionally, conductive traces (not shown) could be provided between one or more of the tamper-detect sensors and the inner surface of the enclosure.

As noted above, in one or more implementations, the inner-sidewall tamper-detect sensor 710 and inner main surface tamper-detect sensor 720 may each include one or more tamper-detect networks, such as one or more unexposed tamper-detect networks formed by circuit lines on one or more flexible layers, such as described herein. The one or more tamper-detect networks may be electrically connected to appropriate monitor circuitry (not shown) disposed within, for instance, the secure volume 805 defined within tamper-respondent assembly 800. As noted, in this example, inner-sidewall tamper-detect sensor 710 and inner main surface tamper-detect sensor 720 are discrete, first and second tamper-detect sensors that overlap, at least in part, and facilitate defining the secure volume about the at least one electronic component 803 to be protected. For instance, the secure volume may be defined by securing the electronic enclosure to a multilayer circuit board 830 with an embedded tamper-detect sensor 831, such as described above. In this example, inner-sidewall tamper-detect sensor 710 is bonded via adhesive 840 to an inner-sidewall surface of the electronic enclosure, wrapping partially around and over, onto the inner main surface of the electronic enclosure as shown. This allows an overlap region of the inner-sidewall tamper-detect sensor 710 and inner main surface tamper-detect sensor 720 to occur at the flat, inner main surface portion of the structure 801. Adhesive 850 is provided to bond inner main surface tamper-detect sensor 720 to the inner main surface of structure 801, as well as to the inner-sidewall tamper-detect sensor 720 in the overlap region. As noted, adhesives 840, 850 may be the same or different adhesives. In one or more implementations, one or both of adhesives 840, 850 may be a thermoset material, such as a thermally conductive epoxy.

As described herein, to provide enhanced tamper-detect protection, one or more conductive traces 820 may be provided disposed, at least in part, on one or more tamper-detect sensors 710, 720 of the tamper-respondent assembly 800. By way of example, a single conductive trace 820 is illustrated in the overlap region, between inner-sidewall tamper-detect sensor 710 and inner main surface tamper-detect sensor 720. In one or more implementations, the conductive trace 820 in the bond region may be formed of a chemically compromisible or dissolvable conductive material, susceptible to wetting or other damage during a chemical attack on adhesive 850 in direct contact therewith. The damage may result in dissolving one or more portions of the conductive trace, and thus, one or more portions of the associated tamper-detect network(s) defined (at least in part) by the trace, and being monitored by the tamper-respondent electronic circuit structure, thereby facilitating detecting the tamper event. Note that the chemically-dissolvable conductor used to form the conductive trace may be the same or a different material than the material used to form the unexposed circuit lines defining the one or more tamper-detect networks of the respective tamper-detect sensors. By way of example, the chemically-dissolvable material used to form the conductive trace may include, at least in part, at least one carbon, silver, or carbon-silver. For instance, the conductive trace may be formed of a carbon-loaded conductive material, silver-loaded conductive material, or carbon-silver-loaded conductive material. In one embodiment, the conductive trace may be deposited directly on, for instance, an exterior surface of the inner main surface tamper-detect sensor 720, for instance, about the periphery of the main surface tamper-detect sensor in an area which aligns with a bond region of the tamper-detect sensor, and in particular, aligns to an overlap region of, for instance, inner-sidewall tamper-detect sensor 710, such as described above.

FIG. 9B illustrates again a potential line of attack 860, addressed by the enhanced tamper-respondent assembly of FIGS. 8A-9B. In this example, however, the line of attack 860 is attempted through structure 801 by milling the upper surface of the structure down to expose adhesive 850. The attack may involve, for instance, a mechanical prying attack against the bond line in the overlap region in order to, for instance, separate inner main surface tamper-detect sensor 720 from inner-sidewall tamper-detect sensor 710, and thereby gain access to the secure volume. Any such attack would preferably damage the conductive trace in multiple locations to facilitate detection of the tamper event by the monitor circuitry, and thus, initiation of an alarm and/or triggering of an erasure of, for instance, an encryption/decryption key or other confidential information stored within the secure volume.

As a tamper-detect enhancement against a mechanical prying force at the bond line between, for instance, inner main surface tamper-detect sensor 720 and inner sidewall tamper-detect sensor 710, the overlap subassembly, which includes the bond line, may be configured with multiple regions of increased susceptibility to breaking of the conductive trace with a tamper event through the subassembly. Various approaches to forming the multiple regions of increased susceptibility to breaking are described below with reference to FIGS. 10A-11B. These approaches are presented by way of example only.

In general, disclosed herein are enhanced tamper-respondent assemblies and fabrication processes, where the above-discussed conductive trace is made more susceptible to breaking or tampering during a tamper event at the bond interface, for instance, between two tamper-detect sensors. For example, in one or more embodiments, a tamper-respondent assembly is provided which includes a tamper-detect sensor, at least one conductive trace, and an adhesive. The tamper-detect sensor facilitates defining a secure volume about at least one electronic component to be protected, and the at least one conductive trace forms, at least in part, at least one tamper-detect network of the tamper-respondent assembly. The conductive trace(s) is disposed, at least in part, on the tamper-detect sensor. The adhesive is disposed, at least in part, between and couples a surface of the tamper-detect sensor to another surface of the tamper-respondent assembly. Together, the tamper-detect sensor, at least one conductive trace, and adhesive form a subassembly of the tamper-respondent assembly, and the subassembly is configured with multiple regions of increased susceptibility to breaking of the at least one conductive trace with an attempted tamper event through the subassembly.

In one or more implementations, the multiple regions of increased susceptibility to breaking of the at least one conductive trace may include multiple regions of the subassembly where a bond interface of the at least one conductive trace to the tamper-detect sensor is different from multiple other regions of the subassembly. For instance, the multiple regions of the subassembly may include multiple regions of reduced bond strength of the at least one conductive trace to the tamper-detect sensor, compared with the multiple other regions of the subassembly. In one or more embodiments, a release agent may be provided in the multiple regions of the subassembly at the bond interface of the conductive trace(s) to the tamper-detect sensor. In such embodiments, the release agent provides the multiple regions of the subassembly with increased susceptibility to breaking of the conductive trace(s). By way of example, the release agent may include an agent selected from the group consisting of wax, polytetrafluoroethylene, silicone, and hydrophobic silanes.

In one or more other implementations, the multiple regions may include multiple non-plasma-cleaned surface regions of the tamper-detect sensor, and the multiple other regions may include multiple plasma-cleaned surface regions of the tamper-detect sensor. As will be understood by one skilled in the art, plasma-cleaning an exterior surface of the tamper-detect sensor facilitates adhesion of the conductive trace to the exterior surface, and thus, by providing multiple non-plasma-cleaned surface regions of the tamper-detect sensor, the conductive trace will adhere less strongly to the exterior surface of the tamper-detect sensor in those regions than in the multiple plasma-cleaned surface regions.

In one or more other implementations, the multiple regions of increased susceptibility to breaking may be defined by varying a bond line thickness of the adhesive disposed, at least in part, over and contacting the at least one conductive trace in order to create stress risers or fracture points at the multiple regions of the subassembly.

Further, in one or more embodiments, the multiple regions of increased susceptibility to breaking of the at least one conductive trace may be spaced along the at least one conductive trace. For instance, the multiple regions may be spaced uniformly along the length of the conductive trace(s), or if desired, in a varying pattern, or even randomly.

As noted, in one or more implementations, the conductive trace may be located in a bond region between first and second tamper-detect sensors, such as disclosed herein.

Figure 10A:
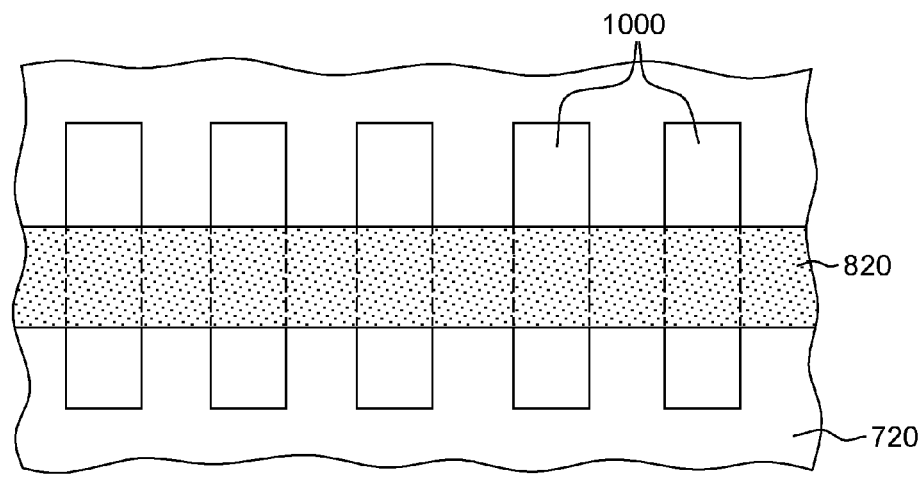
FIG. 10A is a plan view of one embodiment of a conductive trace and tamper-detect sensor subassembly of a tamper-respondent assembly, such as depicted in FIGS. 8A-9A, with the subassembly being configured with multiple regions of increased susceptibility to breaking of the conductive trace with a tamper event into the tamper-respondent assembly at a bond line of the subassembly to another surface of the tamper-respondent assembly, in accordance with one or more aspects of the present invention.

FIG. 10A is a plan view of a conductive trace 820 and tamper-detect sensor 720 subassembly of a tamper-respondent assembly, such as described herein. As illustrated, the subassembly is configured with multiple regions 1000, where the conductive trace is more susceptible to breaking in the presence of a tamper event through an adhesive interface of the subassembly where bonded to another surface within the tamper-respondent assembly, such as described herein. The multiple regions 1000 may be multiple interface regions of the conductive trace 820 to tamper-detect sensor 720, with the regions being sized and positioned to, for instance, intersect the conductive trace 820. In one or more implementations, the regions 1000 may intersect at any angle, with the transverse intersection of FIG. 10A being depicted by way of example only. In one or more implementations, regions 1000 have a length which is equal to or greater than the width of conductive trace 820, as illustrated.

Figure 10B:
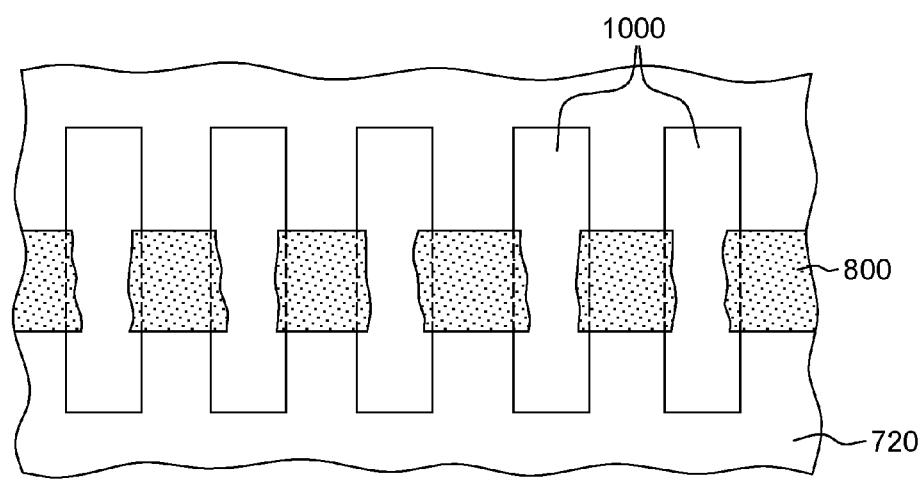
FIG. 10B depicts the subassembly of FIG. 10A, illustrating multiple breaks in the conductive trace based on an attempted tamper event into the tamper-respondent assembly at the bond line of the subassembly to another surface of the tamper-respondent assembly, in accordance with one or more aspects of the present invention.

In one or more embodiments, regions 1000 may be defined by providing a release agent, such as a wax, polytetrafluoroethylene, silicone, etc., on the exterior surface of tamper-detect sensor 720 before conductive trace 820 is deposited, for instance, by silk screening of the trace onto the exterior surface. In this manner, with an attempted mechanical tampering or prying of the adhesive interface, such as described above in connection with FIGS. 9A & 9B, the conductive trace will have an increased susceptibility to breaking or lifting off in regions 1000, as illustrated in FIG. 10B. This is because the bond strength of conductive trace 820 to tamper-detect sensor 720 will be lower in the multiple regions 1000 due to the presence of the release agent, thereby allowing the conductive trace 820 to more readily break in multiple places with the mechanical tamper event against adhesive 850 (FIGS. 9A & 9B).

In one or more other implementations, the fabrication process may be modified by, for instance, masking multiple regions 1000 on the exterior surface of tamper-detect sensor 720, and then, for instance, cleaning the exterior surface of the sensor to facilitate adhesion of the conductive trace 820 (and/or the adhesive 850 (FIGS. 9A & 9B)) to the tamper-detect sensor. In one or more embodiments, the surface may be cleaned, for instance, by a plasma cleaning process which slightly roughens the exterior surface of the tamper-detect sensor 720, which allows the conductive trace to adhere better, that is, have a greater bond strength to the exterior surface of the tamper-detect sensor. After cleaning the exterior surface, then the masking over of multiple regions 1000 may be removed (e.g., dissolved or etched away, or peeled away, or separated), resulting in regions 1000 being non-plasma-cleaned regions, to which the conductive trace does not adhere as readily as in the plasma-cleaned regions. Thus, during an attempted mechanical tamper event through the bond region noted above, the conductive trace will tend to break at the bond interface in the multiple regions 1000, thereby facilitating detection of the event by the monitor circuitry, and thus, initiation of an alarm and/or trigger of an erasure of, for instance, stored confidential information within the secure volume.

Figure 11A:
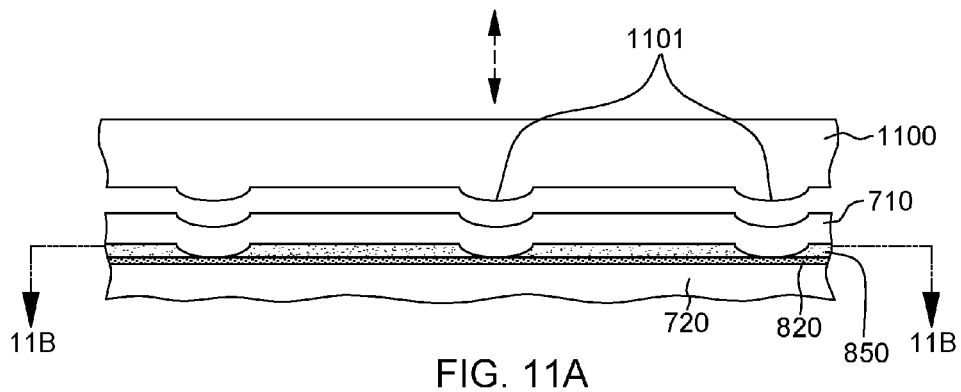
FIG. 11A is a cross-sectional elevational view of an alternate approach for configuring a subassembly, which includes first and second tamper-detect sensors, an adhesive, and a conductive trace, with multiple regions of increased susceptibility to breaking of the conductive trace with a tamper event through the subassembly, in accordance with one or more aspects of the present invention.
Figure 11B:
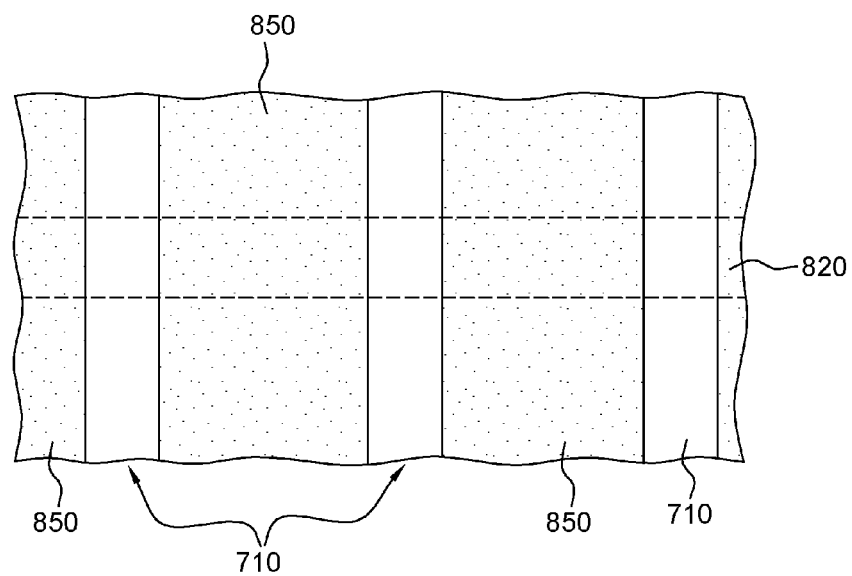
FIG. 11B depicts a cross-sectional plan view of the subassembly of FIG. 11A, taken along line 11B-11B thereof, in accordance with one or more aspects of the present invention.

FIGS. 11A & 11B depict an alternate approach to forming the multiple regions of increased susceptibility to breaking of the at least one conductive trace with a mechanical tamper event through the bond region, such as the above-discussed bond between tamper detect sensors.

Referring collectively to FIGS. 11A & 11B, during assembly, a pusher 1100 with ridges or lands 1101 of desired configuration, size, and protrusion, may be used to (in part) form regions in the overlap subassembly, which have a reduced or varying bond line 850 thickness. The varying bond line thicknesses in the deposited regions creates stress risers or stress concentrators that provide multiple fracture points that have increased susceptibility to breaking with an attempted tamper event through the bond interface between (for example) inner main surface tamper-detect sensor 720 and inner-sidewall tamper-detect sensor 710. Note that in one or more other embodiments, the size, shape and configuration of ridges 1101 on pusher 1100 may vary as desired to define a desired number of regions with fracture points within the bond line resulting in the increased susceptibility to breaking of the conductive trace in the multiple regions of the overlap subassembly.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), and "contain" (and any form contain, such as "contains" and "containing") are open-ended linking verbs. As a result, a method or device that "comprises", "has", "includes" or "contains" one or more steps or elements possesses those one or more steps or elements, but is not limited to possessing only those one or more steps or elements. Likewise, a step of a method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts, and equivalents of all means or step plus function elements in the claims below, if any, are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the invention for various embodiments with various modifications as are suited to the particular use contemplated.

What is claimed is:

1. A tamper-respondent assembly comprising:
   a tamper-detect sensor to facilitate defining a secure volume about at least one electronic component to be protected;
   at least one conductive trace forming, at least in part, at least one tamper-detect network of the tamper-respondent assembly, the at least one conductive trace being exposed, at least in part, on the tamper-detect sensor;
   an adhesive contacting the at least one conductive trace on the tamper-detect sensor, the adhesive being disposed, at least in part, between and coupling a surface of the tamper-detect sensor to another surface of the tamper-respondent assembly; and
   the tamper-detect sensor, at least one conductive trace, and adhesive being a subassembly of the tamper-respondent assembly, the subassembly being configured with multiple regions of increased susceptibility to breaking of the at least one conductive trace with a tamper event through the subassembly.

2. The tamper-respondent assembly of claim 1, wherein the multiple regions of increased susceptibility to breaking of the at least one conductive trace comprise multiple regions of the subassembly where a bond interface of the at least one conductive trace to the tamper-detect sensor is different from multiple other regions of the subassembly.

3. The tamper-respondent assembly of claim 2, wherein the multiple regions of the subassembly comprise multiple regions of reduced bond strength of the at least one conductive trace to the tamper-detect sensor, compared with the multiple other regions of the subassembly.

4. The tamper-respondent assembly of claim 3, further comprising a release agent in the multiple regions of the subassembly at the bond interface of the at least one conductive trace to the tamper-detect sensor, the release agent facilitating the multiple regions of the subassembly with having the increased susceptibility to breaking of the at least one conductive trace.

5. The tamper-respondent assembly of claim 4, wherein the release agent comprises an agent selected from the group consisting of wax, polytetrafluorethylene, silicone, and hydrophobic silanes.

6. The tamper-respondent assembly of claim 3, wherein the multiple regions comprise multiple non-plasma-cleaned surface regions of the tamper-detect sensor, and the multiple other regions comprise multiple plasma-cleaned surface regions of the tamper-detect sensor, the at least one conductive trace adhering stronger to the tamper-detect sensor in the multiple plasma-cleaned surface regions than the multiple non-plasma-cleaned surface regions.

7. The tamper-respondent assembly of claim 1, wherein the multiple regions of increased susceptibility to breaking are defined by a varying bond line thickness of the adhesive disposed over, at least in part, and contacting the at least one conductive trace.

8. The tamper-respondent assembly of claim 1, wherein the multiple regions of increased susceptibility to breaking of the at least one conductive trace are spaced apart along the at least one conductive trace.

9. The tamper-respondent assembly of claim 1, wherein the at least one tamper-detect sensor comprises a first tamper-detect sensor, and the tamper-respondent assembly further comprises a second tamper-detect sensor, the another surface of the tamper-respondent assembly being a surface of the second tamper-detect sensor.

10. The tamper-respondent assembly of claim 9, wherein the first tamper-detect sensor comprises at least one first flexible layer with tamper-detect circuit lines, and the second tamper-detect sensor comprises at least one second flexible layer with tamper-detect circuit lines.

11. A tamper-respondent assembly comprising:
    an electronic enclosure to enclose, at least in part, at least one electronic component to be protected, the electronic enclosure comprising an inner surface;
    a tamper-detect sensor comprising at least one flexible layer with tamper-detect circuit lines, the tamper-detect sensor covering, at least in part, the inner surface of the electronic enclosure and facilitating defining a secure volume about the at least one electronic component;
    at least one conductive trace forming, at least in part, at least one tamper-detect network of the tamper-respondent assembly, the at least one conductive trace being exposed, at least in part, on the tamper-detect sensor;
    an adhesive contacting the at least one conductive trace on the at least one tamper-detect sensor, the adhesive being disposed, at least in part, between and coupling a surface of the tamper-detect sensor to another surface of the tamper-respondent assembly; and
    the tamper-detect sensor, at least one conductive trace, and adhesive being a subassembly of the tamper-respondent assembly, the subassembly being configured with multiple regions of increased susceptibility to breaking of the at least one conductive trace with a tamper event through the subassembly.

12. The tamper-respondent assembly of claim 11, wherein the multiple regions of increased susceptibility to breaking of the at least one conductive trace comprise multiple regions of the subassembly where a bond interface of the at least one conductive trace to the tamper-detect sensor is different from multiple other regions of the subassembly.

13. The tamper-respondent assembly of claim 12, wherein the multiple regions of the subassembly comprise multiple regions of reduced bond strength of the at least one conductive trace to the tamper-detect sensor, compared with the multiple other regions of the subassembly.

14. The tamper-respondent assembly of claim 13, further comprising a release agent in the multiple regions of the subassembly at the bond interface of the at least one conductive trace to the tamper-detect sensor, the release agent facilitating the multiple regions of the subassembly with having the increased susceptibility to breaking of the at least one conductive trace.

15. The tamper-respondent assembly of claim 14, wherein the release agent comprises an agent selected from the group consisting of wax, polytetrafluorethylene, silicone, and hydrophobic silanes.

16. The tamper-respondent assembly of claim 13, wherein the multiple regions comprise multiple non-plasma-cleaned surface regions of the tamper-detect sensor, and the multiple other regions comprise multiple plasma-cleaned surface regions of the tamper-detect sensor, the at least one conductive trace adhering stronger to the tamper-detect sensor in the multiple plasma-cleaned surface regions than the multiple non-plasma-cleaned surface regions.

17. The tamper-respondent assembly of claim 11, wherein the multiple regions of increased susceptibility to breaking are defined by a varying bond line thickness of the adhesive disposed over, at least in part, and contacting the at least one conductive trace.

18. The tamper-respondent assembly of claim 11, wherein the at least one tamper-detect sensor comprises a first tamper-detect sensor, and the tamper-respondent assembly further comprises a second tamper-detect sensor, the another surface of the tamper-respondent assembly being a surface of the second tamper-detect sensor.

19. The tamper-respondent assembly of claim 18, wherein the first tamper-detect sensor comprises at least one first flexible layer with tamper-detect circuit lines, and the second tamper-detect sensor comprises at least one second flexible layer with tamper-detect circuit lines.

20. A method comprising:
  fabricating a tamper-respondent assembly, the fabricating comprising:
    providing a tamper-detect sensor to facilitate defining a secure volume about at least one electronic component to be protected;
    providing at least one conductive trace forming, at least in part, at least one tamper-detect network of the tamper-respondent assembly, the at least one conductive trace being disposed, at least in part, on the tamper-detect sensor;
    providing an adhesive contacting the at least one conductive trace on the tamper-detect sensor, the adhesive being disposed, at least in part, between and coupling a surface of the tamper-detect sensor to another surface of the tamper-respondent assembly; and
    the tamper-detect sensor, at least one conductive trace, and adhesive being a subassembly of the tamper-respondent assembly, the subassembly being configured with multiple regions of increased susceptibility to breaking of the at least one conductive trace with a tamper event through the subassembly.

* * * * *